United States Patent
Yun et al.

(10) Patent No.: US 9,689,000 B2
(45) Date of Patent: Jun. 27, 2017

(54) GENE DELIVERY SYSTEM HAVING ENHANCED TUMOR-SPECIFIC EXPRESSION, AND RECOMBINANT GENE EXPRESSION REGULATING SEQUENCE

(75) Inventors: Chae Ok Yun, Seoul (KR); A-Rum Yoon, Gyeonggi-do (KR)

(73) Assignee: GENEMEDICINE CO., LTD., Seoul (KR)

( * ) Notice: Subject to any disclaimer, the term of this patent is extended or adjusted under 35 U.S.C. 154(b) by 511 days.

(21) Appl. No.: 13/878,266

(22) PCT Filed: Jun. 28, 2011

(86) PCT No.: PCT/KR2011/004693
§ 371 (c)(1),
(2), (4) Date: Apr. 11, 2013

(87) PCT Pub. No.: WO2012/046943
PCT Pub. Date: Apr. 12, 2012

(65) Prior Publication Data
US 2013/0323206 A1 Dec. 5, 2013

(30) Foreign Application Priority Data
Oct. 8, 2010 (KR) .................. 10-2010-0098498

(51) Int. Cl.
*C12N 15/86* (2006.01)
*A61K 35/761* (2015.01)
*C12N 15/85* (2006.01)

(52) U.S. Cl.
CPC ............ *C12N 15/85* (2013.01); *A61K 35/761* (2013.01); *C12N 15/86* (2013.01); *C12N 2710/10332* (2013.01); *C12N 2710/10343* (2013.01); *C12N 2710/10345* (2013.01); *C12N 2810/6018* (2013.01); *C12N 2830/002* (2013.01); *C12N 2830/008* (2013.01); *C12N 2830/15* (2013.01); *C12N 2830/85* (2013.01)

(58) Field of Classification Search
CPC .......... C12N 15/86; C12N 2710/10332; C12N 2710/10343; A61K 35/761
See application file for complete search history.

(56) References Cited

U.S. PATENT DOCUMENTS

| | | | |
|---|---|---|---|
| 6,692,736 B2 | 2/2004 | Yu et al. | |
| 7,575,919 B2* | 8/2009 | Yu et al. | .................... 435/320.1 |
| 2003/0068307 A1 | 4/2003 | Yu et al. | |
| 2005/0186178 A1* | 8/2005 | Ennist | ................. A61K 38/193 424/93.2 |
| 2005/0214923 A1* | 9/2005 | Yu et al. | .................... 435/235.1 |

FOREIGN PATENT DOCUMENTS

WO   WO 98/35028   *   8/1998

OTHER PUBLICATIONS

Kwon et al Clin Cancer Res; 16(24) Dec. 15, 2010, 6071-6082.*
Li et al Mol Cancer Ther. 2003;2:1003-1009.*
Kwon et al Molecular Therapy vol. 17, Supplement 1, May 2009, S186).*
International Search Report for PCT/KR2011/004693.
Cai et al. "Kaposi's Sarcoma-Associated Herpesvirus Latent Protein LANA Interacts with HIF-1alpha to Upreguate RTA Expression during Hypoxia: Latency Control under Low Oxygen Conditions", Journal of Virology, Aug. 2006, vol. 80, No. 16, pp. 7965-7975; See abstract and figure 6.
Papadakis, E. D. et al. "Promoters and Control Elements: Designing Expression Cassettes for Gene Therapy", Current Gene Therapy, Mar. 31, 2004, vol. 4, No. 1, pp. 89-113; See the entire document.

* cited by examiner

*Primary Examiner* — Anoop Singh
(74) *Attorney, Agent, or Firm* — Harness, Dickey & Pierce, P.L.C.

(57) ABSTRACT

The present invention relates to a gene expression regulating sequence consisting of a combination of HRE, E2F and TERT, and to a gene delivery system having significantly improved selective tumor cell cytotoxicity using same, and more particularly, to a recombinant adenovirus. In addition, the present invention relates to a pharmaceutical antitumor composition comprising the recombinant adenovirus. The replication of the recombinant adenovirus of the present invention is tumor-specifically regulated by the novel gene expression regulating sequence of the present invention, thus enabling the recombinant adenovirus of the present invention to exhibit improved selective tumor cell cytotoxicity or apoptotic potential, and exhibit remarkably improved antitumor effects particularly in hypoxic conditions. In addition, the specific expression of the recombinant adenovirus in tumor cells may increase in vivo stability, and thus may induce greatly improved antitumor effects.

11 Claims, 19 Drawing Sheets

A. E-Rd19

B. EE-Rd19

C. HE-Rd19

D. HEE-Rd19

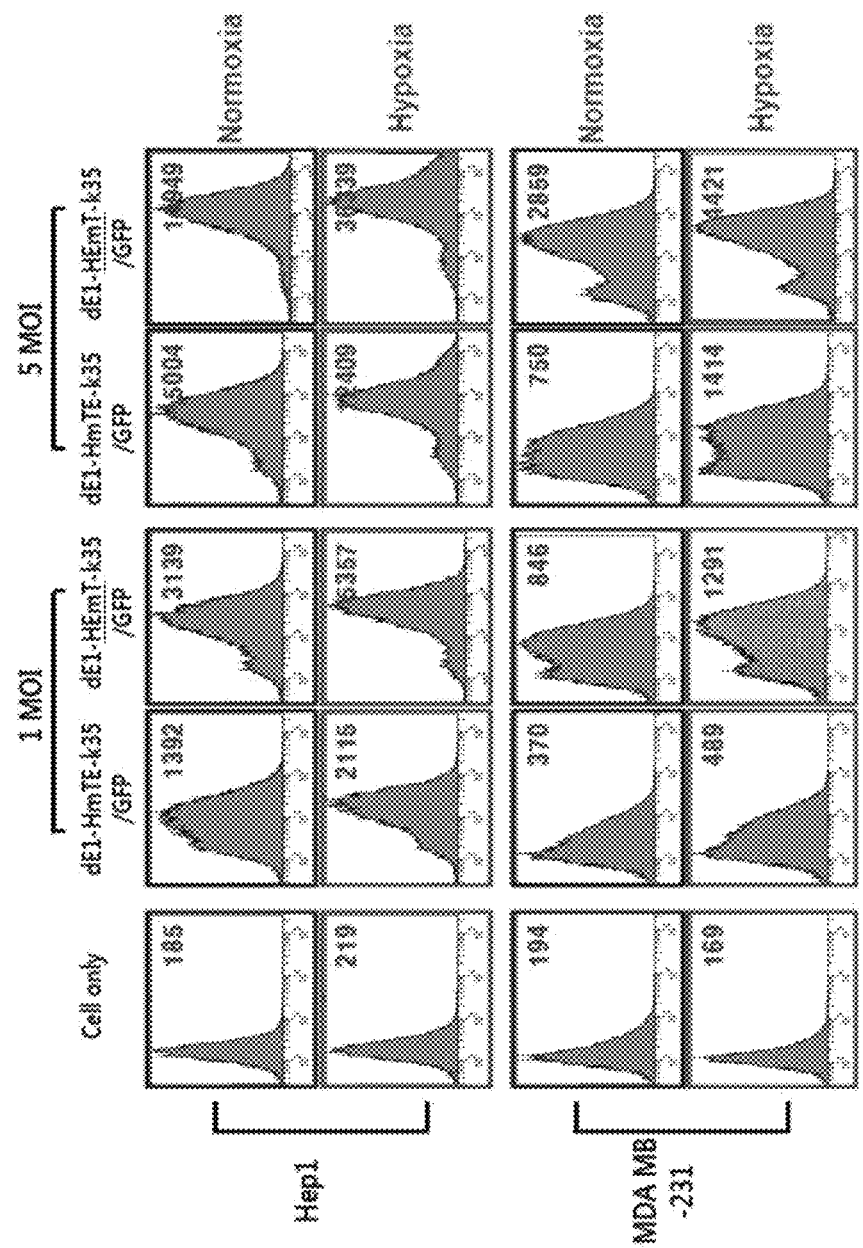

1. A549
2. Rd19-k35
3. Rd19-k35/DCN
4. HEmT-Rd19-k35
5. HEmT-Rd19-k35/DCN

GENE DELIVERY SYSTEM HAVING ENHANCED TUMOR-SPECIFIC EXPRESSION, AND RECOMBINANT GENE EXPRESSION REGULATING SEQUENCE

CROSS REFERENCE TO RELATED APPLICATIONS AND CLAIM OF PRIORITY

This patent application is a National Phase application under 35 U.S.C. §371 of International Application No. PCT/KR2011/004693, filed on Jun. 28, 2011, which claims priority to Korean Patent Application number 10-2010-0098498, filed on Oct. 8, 2010, entire contents of which are incorporated herein by reference.

REFERENCE TO A SEQUENCE LISTING

This application contains references to nucleic acid sequences which have been submitted concurrently herewith as the sequence listing text file "61652987_1.txt", file size 2 KiloBytes (KB), created on 4 Jan. 2016. The aforementioned sequence listing is hereby incorporated by reference in its entirety pursuant to 37 C.F.R. §1.52(e)(5).

FIELD OF THE INVENTION

The present invention relates to a gene delivery system having a recombinant gene expression regulatory sequence with improved tumor-specific expression.

DESCRIPTION OF THE RELATED ART

A growth of malignant tumor is largely influenced by nutrients and oxygen supply. Particularly, oxygen is an absolutely necessary material for suitable energy metabolism in tumor cells.

Typically, hypoxia due to rapidly growing tumor easily occurs in the center of tumor. This hypoxia is a very important element in the tumor treatment and tumor progression. Hypoxia region in solid tumor promotes motility and angiogenesis for survival and metastasis of tumor cells to favorably act in tumor progression. In addition, recent studies have been reported that where tumor cells are undergone hypoxia, apoptosis is suppressed by increasing the expression of anti-apoptosis material and the tumor cells have resistance to radiotherapy and chemotherapy. As the anti-tumor treatments show limitations, novel anti-tumor therapeutic methods are urgently needed in order to overcome the limitations. Therefore, currently, various methods using virus have been developing for effective tumor treatments. As a representative of the methods, current clinical trials using adenovirus have been actively developing. The recombinant adenovirus shows excellent gene delivery efficiency in various cell types regardless of cell division states, can easily produce high titers of virus. It is easy to delivery gene in vivo as well as to be easily concentrated. In addition, where tumor is treated with gene therapy, there is no need to express therapeutic genes in long-term or consistently. Furthermore, the host's immune response induced by virus itself for treating does not greatly matter. Therefore, adenoviral gene delivery system for tumor therapy is drawing attentions. Based on these advantages, the frequency in the use of recombinant adenovirus for gene therapy against tumor is constantly increasing in recent years. Particularly, studies for oncolytic recombinant adenovirus which is selectively replicated only in tumor cells to kill tumor cells are variously researched. The oncolytic adenovirus, which is selectively replicated in tumor cells to selectively kill tumor cells, can secondarily infect tumor cells which are existed in around the primary infected tumor cells as well as primary infected tumor cells by viral replication to enhance therapeutic effects. There is an additional advantage that the toxicity by adenovirus is decreased in the surrounding normal cells since the oncolytic adenoviral replication is inhibited. In addition, recombinant adenovirus is developed by inserting tumor-specific gene regulatory region into E1 gene region to replicate for selectively targeting tumor cells. For these reasons, it is expected that the clinical trial applicability of the oncolytic adenovirus is likely to increase gradually. Under oxygen-deficient environment in tumor, HIF-1α (hypoxia-inducible factor-1α) and p21$^{cip1}$ (Cyclin-dependent kinase inhibitor 1A) are activated and their expressions are increased to inhibit cell cycle, thereby the viral replication is inhibited since it depends on host. It turns out that persistent tumor treatments using virus are limited. However, the promoters or the enhancers of genes regulated by hypoxia are used by counterplotting this limitation such that specificity for tumor cells can be increased. There are also approaches for antitumor treatments through gene therapy: an approach that viral replication is regulated by tumor-specific promoter to selectively kill tumor cells using oncolytic virus; and another approach that therapeutic genes which can induce cell apoptosis in tumor cells are delivered.

E2F is one of oncogenes and known to be highly expressed in several types of tumor cells. It binds to pRb (retinoblastoma protein) such that its activity is inhibited. It is known that E2F released from pRb is a transcription factor to promote the transcription of several genes supervising cell cycle progress as well as the activation of adenovirus E2 promoter. Meanwhile, oxygen-deficient region commonly exists in solid tumor and this hypoxia induces productions of survival factors such as glycolytic enzyme and proangiogenic factor, whereby various tumors under hypoxia are given a resistance to radiotherapy or chemotherapy. In particular, the hypoxic tumors react to hypoxia to produce HIF. HIF binds to HRE (hypoxia-response elements) to activate transcription of angiogenesis gene such as VEGF existing downstream of HIF. Based on this fact, the present inventors have previously developed the oncolytic adenovirus E-Rd19 and they have verified tumor cell killing effects in order to construct oncolytic adenovirus in which E1 expression of adenovirus is regulated by E2F promoter and HRE enhancer. In addition to this, the present inventors have developed oncolytic adenovirus EE-Rd19 and HE-Rd19 having modified E2F promoter.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY

The present inventors have made intensive researches to develop a therapeutic agent with better improved oncolytic activity through excellent tumor-specific gene delivery efficiency. As a result, they have found that where adenovirus including expression regulatory sequence consisting of a HRE enhancer, an E2F promoter and a TERT promoter is used, oncolytic activity is significantly increased.

Accordingly, it is an object of this invention to provide a gene delivery system with improved tumor-specific expression.

It is another object of this invention to provide a recombinant adenovirus with improved oncolytic activity.

It is still another object of this invention to provide an antitumor composition comprising a therapeutically effective amount of the recombinant adenovirus.

Other objects and advantages of the present invention will become apparent from the detailed description to follow taken in conjugation with the appended claims and drawings.

In one aspect of the present invention, there is provided a gene expression regulatory sequence, comprising:

(i) a HRE (hypoxia-response elements) enhancer sequence; and (ii) an E2F promoter sequence wherein the E2F promoter is positioned downstream of the HRE enhancer sequence, whereby the HRE enhancer sequence and the E2F promoter cooperatively trigger the expression of a gene.

The present inventors have made intensive researches to develop a therapeutic agent with better improved oncolytic activity through excellent tumor-specific gene delivery efficiency. As a result, they have found that where adenovirus including expression regulatory sequence consisting of HRE enhancer, E2F promoter and TERT promoter is used, oncolytic activity is significantly increased.

The term used herein "E2F promoter sequence" refers to promoter of E2F gene as transcription factor promoting adenovirus E2 promoter and transcription of several genes supervising cell cycle progress. E2 is an oncogene and binds to pRb (retinoblastoma protein), resulting in inhibition of its activity.

According to a preferred embodiment, E2 promoter sequence used in the present invention includes the nucleotide sequence as set forth in SEQ ID NO:1. More preferably, E2 promoter repeat sequence is used to enhance tumor-specific expression. The repeat sequence used in the present invention may comprise a continuously repeated sequence in which an identical sequence is continuously repeated in an immediately adjacent manner, or a discontinuously repeated sequence in which an identical sequence is discontinuously repeated with intervention of a nucleotide linker in a suitable length not affecting activities of promoters or enhancer.

Still more preferably, E2F sequence used in the present invention comprises a sequence in which the nucleotide sequence of SEQ ID NO:1 is repeated 2-10 times, still much more preferably 2-7 times, and most preferably 2 times.

The term used herein "HRE enhancer sequence" refers to hypoxia-response enhancer sequence. Certain genes expressions in cells are regulated under hypoxia condition (Bunn and Poyton, Physiol. Rev. 76:839-885 (1996); Dachs and Stratford Br. J. Cancer 74:5126-5132 (1996); Guillemin and Krasnow, Cell 89:9-12 (1997)). Blood supply in most of tumor cells is insufficient since tumor cells typically grow faster than endothelial cells generating blood vessels such that hypoxia is induced in tumor cells. Oxygen-deficient region commonly exists in solid tumor and this hypoxia induces productions of survival factors such as glycolytic enzyme and proangiogenic factor, whereby various tumors under hypoxia are given a resistance to radiotherapy or chemotherapy. Therefore, the present inventors have developed oncolytic adenovirus in which adenovirus E1 expression is regulated by E2F promoter and HRE enhancer.

Major mediator of hypoxia response is HIF-1α (hypoxia inducible factor-1α) and it interacts with HRE in regulatory region of a variety of genes. The genes include VEGF (vascular endothelial growth factor) gene, enolase-1 and GAPDH (glyceraldehyde-3-phosphate dehydrogenase).

Like this, the present invention uses HRE which regulates expression of genes and interact with HIF-1α under hypoxia condition. HRE significantly enhances tumor cell-specificity of gene delivery system, particularly, recombinant adenovirus.

According to a preferred embodiment, HRE sequence used in the present invention includes the nucleotide sequence as set forth in SEQ ID NO:2. More preferably, HRE repeat sequence is used to enhance transcription activity by HRE sequence. Still more preferably, HRE sequence used in the present invention includes the nucleotide sequence as set forth in SEQ ID NO:2 repeated 2-20 times, still much more preferably 3-8 times, and most preferably 6 times.

According to a preferred embodiment, the gene expression regulatory sequence further includes TERT (telomere reverse transcriptase) promoter sequence.

TERT is a component of telomerase and known to be involved in cell aging, tumor and cell immortality (Counter, C M et al. EMBO J. 11, 1921-29 (1992), Kim. N W et al. Science, 21:2011-5 (1994), Harley, C B et al. Nature, 345:458-60 (1990)).

Telomerase activity is observed in human ovarian and testicular germ cells and lymphocytes, however, it is not observed in other normal somatic cells (Wright, W E et al. Dev Genet 18:173-9 (1996)). Therefore, normal somatic cells is not longer divide and die since telomere length is reduced to less than certain length after limited number of cell division (Yasumoto, S. et al. Oncogene. 3:433-9 (1996)). In contrast, telomerase activity is increased in benign tumor cells and tumor cells (Broccoli, D. et al. Proc.: Natl. Acad Sci. USA 92:9082-6 (1995). Increase of telomerase activity in ovarian cancer has been first reported. There are many reports that increase of telomerase activity is nearly observed in all human cancer such as blood cancer, gastric cancer, lung cancer, liver cancer, colon cancer, brain cancer, prostate cancer, head and neck cancer, and breast cancer (Counter, C M et al. Proc Natl. Acad Sci. USA 91:2900-4 (1994)). TRET expression plays a role in telomerase function and it is related to telomerase activity. Recently, it is determined that telomerase expression is regulated by TERT promoter activity, i.e., TERT mRNA level and the minimal promoter size for regulating TERT activity is 181 bp. In the present gene delivery system, TERT enhances tumor cell-specificity. Preferably, the present HRE sequence is the nucleotide sequence as set forth in SEQ ID NO:3.

According to a preferred embodiment, the present gene expression regulatory sequence is inserted into E1 region of a recombinant adenovirus vector and includes the HRE sequence, the E2F promoter and the TERT promoter sequence in a 5' to 3-direction.

Most preferably, the HRE sequence is repeated 6 times and the E2F promoter is repeated 2 times.

In another aspect of the present invention, there is provided a gene delivery system with improved tumor-specific expression, comprising:

(a) the gene expression regulatory sequence according to any one of claims 1 to 6; and (b) a target gene of interest to be expressed operably linked to the gene expression regulatory sequence.

Since the gene expression regulatory sequence of this invention is equal to the gene expression regulatory sequence as described above, the common descriptions between them are omitted in order to avoid undue redundancy leading to the complexity of this specification.

The term used herein "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The gene of interest to be expressed which is operably linked to the gene expression regulatory sequence of the present invention is not particularly limited.

For instance, target gene of interest to be expressed includes genes derived from genome of gene delivery system (e.g., adenovirus E1A gene) or therapeutic transgene. Therapeutic transgene will be described in detail as follows.

According to a preferred embodiment, the gene delivery system is a plasmid, a recombinant adenovirus, an adeno-associated virus, retrovirus, lentivirus, herpes simplex virus, a vaccinia virus, a pox virus, a polymer, a liposome or a niosome.

The gene expression regulatory sequence of the present invention as well as the sequence of gene of interest to be delivered operably linked to the gene expression regulatory sequence may be applied to any of gene delivery systems used in conventional gene therapy, preferably, plasmid, adenovirus (Lockett L J, et al., Clin. Cancer Res., 3:2075-2080 (1997)), adeno-associated virus (AAV, Lashford L S., et al., Gene Therapy Technologies, Applications and Regulations Ed. A. Meager, 1999), retrovirus (Gunzburg W H, et al., Retroviral vectors. Gene Therapy Technologies, Applications and Regulations Ed. A. Meager, 1999), lentivirus (Wang G. et al., J. Clin. Invest. 104(11):R55-62 (1999)), herpes simplex virus (Chamber R., et al., Proc. Natl. Acad. Sci USA, 92:1411-1415 (1995)), vaccinia virus (Puhlmann M. et al., Human Gene Therapy, 10:649-657 (1999)) liposome ((Methods in Molecular Biology, Vol 199, S. C. Basu and M. Basu (Eds.), Human Press 2002)) or niosome. Most preferably, the gene delivery system of this invention is constructed by applying recombinant adenovirus.

i. Adenovirus

Adenoviruses have been usually employed as a gene delivery system because of its mid-sized genome, ease of manipulation, high titer, wide target-cell range, and high infectivity. Both ends of the viral genome contains 100-200 bp ITRs (inverted terminal repeats), which are cis elements necessary for viral DNA replication and packaging. The E1 region (E1A and E1B) encodes proteins responsible for the regulation of transcription of the viral genome and a few cellular genes. The expression of the E2 region (E2A and E2B) results in the synthesis of the proteins for viral DNA replication.

Of adenoviral vectors developed so far, the replication incompetent adenovirus having the deleted E1 region is usually used. The deleted E3 region in adenoviral vectors may provide an insertion site for transgenes (Thimmappaya, B. et al., Cell, 31:543-551 (1982); and Riordan, J. R. et al., Science, 245:1066-1073 (1989)). Therefore, it is preferred that the nucleotide sequence encoding the CCN5 protein or CCN2ΔCT protein of this invention is inserted into either the deleted E1 region (E1A region and/or E1B region, preferably, E1B region) or the deleted E3 region, more preferably, the deleted E3 region. The nucleotide sequence of interest to be delivered is preferably inserted into either the deleted E1 region (E1A region and/or E1B region, preferably, E1B region) or the deleted E3 region, more preferably, the deleted E1 region. Furthermore, the inserted sequences may be incorporated into the deleted E4 region. The term used herein "deletion" with reference to viral genome encompasses whole deletion and partial deletion as well.

In addition, in nature, adenovirus can package approximately 105% of the wild-type genome, providing capacity for about 2 extra kb of DNA (Ghosh-Choudhury et al., EMBO J., 6:1733-1739 (1987)). In this regard, the foreign sequences described above inserted into adenovirus may be further inserted into adenoviral wild-type genome.

The foreign genes delivered by the present adenoviral gene delivery system are episomal, and therefore, have low genotoxicity to host cells. Therefore, gene therapy using the adenoviral gene delivery system of this invention may be considerably safe.

ii. Retrovirus

Retroviruses capable of carrying relatively large exogenous genes have been used as viral gene delivery vectors in the senses that they integrate their genome into a host genome and have broad host spectrum.

To construct a retroviral vector, the target nucleotide sequence of interest to be expressed is inserted into the viral genome in the place of certain viral sequences to produce a replication-defective virus. To produce virions, a packaging cell line containing the gag, pol and env genes but without the LTR (long terminal repeat) and ψ components is constructed (Mann et al., Cell, 33:153-159 (1983)). When a recombinant plasmid containing the target nucleotide sequence of interest to be expressed, LTR and ψ is introduced into this cell line, the ψ sequence allows the RNA transcript of the recombinant plasmid to be packaged into viral particles, which are then secreted into the culture media (Nicolas and Rubinstein "Retroviral vectors," In: Vectors: A survey of molecular cloning vectors and their uses, Rodriguez and Denhardt (eds.), Stoneham: Butterworth, 494-513 (1988)). The media containing the recombinant retroviruses is then collected, optionally concentrated and used for gene delivery.

A successful gene transfer using the second-generation retroviral vector has been reported. Kasahara et al. (Science, 266:1373-1376 (1994)) prepared variants of moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

iii. AAV Vector

Adeno-associated viruses are capable of infecting non-dividing cells and various types of cells, making them useful in constructing the gene delivery system of this invention. The detailed descriptions for use and preparation of AAV vector are found in U.S. Pat. Nos. 5,139,941 and 4,797,368.

Research results for AAV as gene delivery systems are disclosed in LaFace et al, Viology, 162:483486 (1988), Zhou et al., Exp. Hematol. (NY), 21:928-933 (1993), Walsh et al, J. Clin. Invest., 94:1440-1448 (1994) and Flotte et al., Gene Therapy, 2:29-37 (1995). Recently, an AAV vector has been approved for Phase I human trials for the treatment of cystic fibrosis.

Typically, a recombinant AAV virus is made by cotransfecting a plasmid containing the gene of interest (i.e., relaxin gene and nucleotide sequence of interest to be delivered) flanked by the two AAV terminal repeats (McLaughlin et al., 1988; Samulski et al., 1989) and an expression plasmid containing the wild type AAV coding sequences without the terminal repeats (McCarty et al., J. Virol., 65:2936-2945 (1991)).

iv. Other Viral Vectors

Other virus vectors may be used for the gene transduction system in the present invention. Vectors derived from viruses such as vaccinia virus (Puhlmann M. et al., Human Gene Therapy 10:649-657 (1999); Ridgeway, "Mammalian expression vectors," In: Vectors: A survey of molecular cloning vectors and their uses. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. Gene transfer. New York: Plenum Press, 117-148 (1986) and Coupar et al., Gene, 68:1-10 (1988)), lentivirus (Wang G. et al., J. Clin. Invest. 104(11):R55-62 (1999)) and herpes simplex virus (Chamber R., et al., Proc. Natl. Acad. Sci USA 92:1411-1415 (1995)) may be used in the present delivery systems for transferring the target nucleotide sequence into cells.

v. Polymer

Polymeric delivery system has been widely used as non-viral gene delivery system, including gelatin, chitosan (Carreno G B, Duncan R. Evaluation of the biological properties of soluble chitosan and chitosan microspheres. Int J Pharm 148:231-240 (1997)) PLL (poly-LLysine) (Maruyama A, Ishihara T, Kim J S, Kim S W, Akaike T. Nanoparticle DNA carrier with poly (L-lysine) grafted polysaccharide copolymer and poly (D, Llactide). Bioconjugate Chem 8:735-742 (1997)) and PEI (polyethyleneamine) (Abdallah B, Hassan A, Benoist C, Goula D, Behr J P, Demeneix B A A powerful nonviral vector for in vivo gene transfer into the adult mammalian brain: Polyetheleneimine Human Gene Ther 7:1947-1954 (1996)). Advantages of polymeric delivery system are that immune responses and incidence of acute toxicity is low, the preparation is simple, and can be mass-produced.

vi. Liposome

Liposomes are formed spontaneously when phospholipids are suspended in an excess of aqueous medium. Liposome-mediated nucleic acid delivery has been very successful as described in Nicolau and Sene, Biochim. Biophys. Acta, 721:185-190 (1982) and Nicolau et al., Methods Enzymol., 149:157-176 (1987). Example of commercially accessible reagents for transfecting animal cells using liposomes includes Lipofectamine (Gibco BRL). Liposomes entrapping the HIF-2α gene interact with cells by mechanism such as endocytosis, adsorption and fusion and then transfer the sequences into cells.

The methods introduced gene delivery system of the present invention into cells the above-mentioned may be carried out through a variety of methods known in the art. Where the present gene delivery system is constructed on the basis of viral vector construction, the contacting is performed as conventional infection methods known in the art. The infection of hosts using viral vectors is well described in the above-cited publications.

Where the present gene delivery system is a naked recombinant DNA molecule or plasmid, the nucleotide sequence to be delivered are introduced into cells by microinjection (Capecchi, M. R., Cell, 22:479 (1980) and Harland and Weintraub, J. Cell Biol. 101:1094-1099 (1985)), calcium phosphate co-precipitation (Graham, F. L. et al., Virology, 52:456 (1973) and Chen and Okayama, Mol. Cell. Biol. 7:2745-2752 (1987)), electroporation (Neumann, E. et al., EMBO J., 1:841 (1982) and Tur-Kaspa et al., Mol. Cell Biol., 6:716-718 (1986)), liposome-mediated transfection (Wong, T. K. et al., Gene, 10:87 (1980) and Nicolau and Sene, Biochim. Biophys. Acta, 721:185-190 (1982); and Nicolau et al., Methods Enzymol., 149:157-176 (1987)), DEAE-dextran treatment (Gopal, Mol. Cell Biol., 5:1188-1190 (1985)) and particle bombardment (Yang et al., Proc. Natl. Acad. Sci., 87:9568-9572 (1990)).

In still another aspect of the present invention, there is provided a recombinant adenovirus with improved oncolytic activity, comprising:

(a) an ITR (inverted terminal repeat) sequence of adenovirus;

(b) a gene expression regulatory sequence, comprising (i) a HRE (hypoxia-response elements) enhancer sequence; and (ii) an E2F promoter sequence; wherein the E2F promoter is positioned downstream of the HRE enhancer sequence, whereby the HRE enhancer sequence and the E2F promoter cooperatively trigger the expression of a gene.; and (c) a therapeutic transgene selected from a group consisting of a tumor suppressor gene, an antigenic gene, a cytotoxic gene, a cytostatic gene gene, an apoptosis gene and an anti-angiogenic gene.

Since the gene expression regulatory sequence of this invention is equal to the gene expression regulatory sequence as described above, the common descriptions between them are omitted in order to avoid undue redundancy leading to the complexity of this specification.

The gene expression regulatory sequence of this invention may be positioned at upstream of E1A gene in recombinant adenovirus, deleted E3 gene region or both of upstream of E1A gene and deleted E3 gene region.

Where the present gene expression regulatory sequence is positioned at upstream of E1A gene in recombinant adenovirus, i.e., the present gene expression regulatory sequence is operatively linked to E1A gene (HRE-E2F-TERT-E1A), the recombinant adenovirus replication is regulated by the present gene expression regulatory sequence. Where the present gene expression regulatory sequence is positioned at deleted E3 gene region, "gene expression regulatory sequence-transgene-poly A" expression cassette type may be inserted into E3 gene region.

The term used herein "therapeutic transgene" refers to a nucleotide sequence representing therapeutic effects by expressing in tumor cells.

The term used herein "tumor suppressor gene" refers to a nucleotide sequence which capable of suppressing phenotype of the tumor or inducing apoptosis. The useful tumor suppressor genes in the present invention include p53 gene, APC gene, DPC-4/Smad4 gene, BRCA-1 gene, BRCA-2 gene, WT-1 gene, retinal neuroblastoma genes (Lee et al., Nature, 1987, 329,642), MMAC-1 gene, adenomatoid polyps coil protein (adenomatouspolyposis coil protein) (U.S. Patent Publication No. 5783666), DCC gene, MMSC-2 gene, NF-1 gene, tumor suppressors genes located in chromosome 3p21.3 (Cheng et al. Proc. Nat. Acad. Sci, 95:3042-3047 (1998)), MTS1 gene, CDK4 gene, NF-1 gene, NF-2 gene and the VHL gene.

The term used herein "antigenic gene" refers to a nucleotide sequence producing cell surface antigen protein which is expressed in target cell and can be recognized by the immune system. The antigenic genes include carcinoembryonic antigen (CEA), HER-2, PSA (prostate specific antigen) and p53 (Levine, A., WO94/02167). For recognizing immune system, the antigenic gene may be combined to MHC type I antigen.

The term used herein "cytotoxic gene" refers to a nucleotide sequence representing cytotoxicity by expressing in cells. The cytotoxic genes include a nucleotide sequence coding for Pseudomonas exotoxin, ricin toxin, diphtheria toxin, CD (cytosine deaminase), TK (thymidine kinase).

The term used herein "cytostatic gene" refers to a nucleotide sequence arrest ting cell cycle during cell cycling by expressing in cells. The cytostatic genes include p21, retinal neuroblastoma gene, E2F-Rb fusion protein gene, gene coding for cyclin-dependent kinase inhibitor (e.g., p16, p15, p18, and p19), growth arrest specific homeobox (GAX) genes (International patent Publication WO 97/16459 and WO96/30385), but is not limited thereto.

The term used herein "apoptotic gene" refers to a nucleotide sequence inducing apoptosis by expressing in cells. The apoptotic genes include p53, adenovirus E3-11.6K (derived from Ad2 and Ad5) or adenovirus E3-10.5K (derived from Ad), adenovirus E4 gene, p53 pathway gene and gene coding for caspase.

The term used herein "anti-angiogenic gene" refers to a nucleotide sequence releasing anti-angiogenic factors out of cells. The anti-angiogenic genes include inhibitory factor of vascular endothelial growth factor (VEGF) such as angiostatin and Tie2 (PNAS, 95:8795-800 (1998)) as (VEGF), and endostatin.

It is preferred that the transgene inserted into recombinant adenovirus is inserted into expression cassette of promoter-transgene-poly A sequence. As The promoter, the present gene expression regulatory sequence (HRE-TERT, HRE-E2F, HRE-TERTE2F or HRE-E2F-TERT) conventional promoter may be used. The conventional promoter linked to the transgene is operable in, preferably, animal, more preferably, mammalian cells, to control transcription of the transgene, including the promoters derived from the genome of mammalian cells or from mammalian viruses, for example, CMV (cytomegalovirus) promoter, CII promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, inducible promoter, tumor cell specific promoter (e.g., TERT promoter, PSA promoter, PSMA promoter, CEA promoter, E2F promoter and AFP promoter) and tissue specific promoter (e.g., albumin promoter), but is not limited thereto.

It is preferred that the expression constructs used in the present invention comprises polyadenylated sequence. The polyadenylated sequences include bovine growth hormone terminator (Gimmi, E. R., et al., Nucleic Acids Res. 17:6983-6998 (1989)), polyadenylated sequence derived from SV40 (Schek, N, et al., Mol. Cell Biol. 12:5386-5393 (1992)), HIV-1 polyA (Klasens, B. I. F., et al., Nucleic Acids Res. 26:1870-1876 (1998)), β-globin polyA (Gil, A., et al, Cell 49:399-406 (1987)), HSV TK polyA (Cole, C. N. and T. P. Stacy, Mol. Cell. Biol. 5:2104-2113 (1985)) or polyomavirus polyA (Batt, D. B and G. G. Carmichael, Mol. Cell. Biol. 15:4783-4790 (1995)), but is not limited thereto.

Most preferably, the present therapeutic transgene is one or more selected from a group consisting of LK 8 (Apolipoprotein Klingle 8) gene, CD (cytosine kinase) gene, TK (thymidine kinase) gene and decorin gene.

Decorin inhibits the activity of TGF (tumor growth factor)-β to protect collagen fibrosis, is involved in matrix assembly and inhibits tumor cell growth to act natural antagonist in tumor formation and growth.

LK8 (Apolipoprotein Klingle 8) inhibits proliferation of vascular endothelial cells.

TK is thymidine and nucleotide analogues and can phosphorylate ganciclovir used as an antiviral agent. Phosphorylated ganciclovir-triphosphate is inserted into DNA strand during DNA synthesis to disrupt the formation of DNA strand, finally resulting in inhibition of DNA synthesis. In addition, living tumor cells phagocyte dead tumor cells such that non-inserted-HSV-TK tumor cells are obtained ganciclovir-triphosphate and occur cell death to be induce bystander effect. The bystander effect also can be occurred by inducing tumor cell-specific immune response due to tumor cell killing.

CD (cytosine deaminase) converts non-toxic 5-FC (5-fluorocytosine) to 5-FU (5-fluorouracil) having strong cytotoxicity and radiosensitivity.

In further aspect of the present invention, there is provided an antitumor composition comprising: (a) a therapeutically effective amount of the recombinant adenovirus according to any one of claims 10-16; and (b) a pharmaceutically acceptable carrier.

In still further aspect of the present invention, there is provided a method for treating a tumor, comprising administering an antitumor composition comprising a therapeutically effective amount of the recombinant adenovirus according to any one of claims 10-16 to a mammalian subject in need thereof.

Since the recombinant adenovirus contained the present composition has oncolytic effect to a wide variety of tumor cells, the pharmaceutical composition of this invention is useful in treating tumor-related diseases, including stomach cancer, lung cancer, breast cancer, ovarian cancer, liver cancer, bronchogenic cancer, nasopharyngeal cancer, laryngeal cancer, pancreatic cancer, bladder cancer, colon cancer, and uterine cervical cancer. The term used herein "treatment" refers to (i) suppression of disease or disorder development; (ii) alleviation of disease or disorder; and (iii) curing of disease or disorder. Therefore, the term "therapeutically effective amount" as used herein means an amount sufficient to achieve the pharmaceutical effect described above.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative.

The pharmaceutical composition according to the present invention may be preferably administered parenterally, i.e., by intravenous, intraperitoneal, intratumoral, intramuscular, subcutaneous, intracardiomuscular or local administration. For example, the pharmaceutical composition may be administered intraperitoneally to treat ovarian cancer and intravenously to treat liver cancer, directly injected to visible tumor mass to treat breast cancer, directly injected to enema to treat colon cancer, and directly injected to a catheter to treat bladder cancer.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, the pharmaceutical composition of the present invention comprises $1\times10^5-1\times10^{15}$ pfu/ml of a recombinant adenovirus, and $1\times10^{10}$ pfu of a recombinant adenovirus is typically injected once every other day over two weeks.

According to the conventional techniques known to those skilled in the art, the pharmaceutical composition comprising the recombinant adenovirus according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The pharmaceutical composition comprising the recombinant adenovirus according to the present invention may be utilized alone or in combination with typical chemotherapy or radiotherapy. Such combination therapy may be more effective in treating cancer. The chemotherapeutic agents useful for the combination therapy include cisplatin, carboplatin, procarbazine, mechlorethamine, cyclophosphamide, ifosfamide, melphalan, chlorambucil, bisulfan, nikosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. Examples of the radiotherapy useful for the combination therapy include X-ray illumination and γ-ray illumination.

According to a preferred embodiment, the composition further includes GCV (ganciclovir) as an active ingredient. GCV is a purine-based compound for the prevention and treatment of CMV (cytomegalovirus) infection as antiviral agent. HSV-TK phosphorylates non-toxic prodrug ganciclovir (GCV) to inhibit DNA synthesis of infected cells, whereby dividing cells can be selectively killed. Thymidine kinase (TK) is an enzyme used for DNA synthesis in salvage pathway. HSV-TK is thymidine and nucleotide analogues and can phosphorylate ganciclovir used as an antiviral agent. Phosphorylated ganciclovir-triphosphate is inserted into DNA strand during DNA synthesis to disrupt the formation of DNA strand, finally resulting in inhibition of DNA synthesis. In addition, living tumor cells phagocyte dead tumor cells such that non-inserted-HSV-TK tumor cells are obtained ganciclovir-triphosphate and occur cell death to be induce bystander effect. Therefore, the present composition may be used for antitumor composition with the maximizing anti-tumor activity.

Since the present composition includes simultaneously the gene delivery system and GCV, the present composition may be utilized alone. In addition, the present gene delivery system and GCV may be coadministrated separately as separate form, respectively.

The features and advantages of this invention will be summarized as follows:

(a) The present invention provides a gene expression regulatory sequence consisting of a HRE enhancer, an E2F promoter and a TERT promoter, and a gene delivery system with better improved oncolytic activity (b) The present invention shows higher antitumor effects under hypoxia condition. In addition, by TK gene insertion and GCV coadministration, the present invention significantly improve the shortcomings that the biggest limitation of current tumor gene therapy is not inserted therapeutic gene to all tumors.

BRIEF DESCRIPTION OF THE DRAWINGS

FIGS. 9a-b represents results of comparison on gene delivery efficiency of dE1-HmTE-k35/GFP and dE1-HEmT-k35/GFP adenovirus in various tumor cell lines (Number in the box is fluorescence intensity).

DETAILED DESCRIPTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparation of Vector for E-Rd19, EE-Rd19, HE-Rd19 and HEE-Rd19

To construct adenovirus having an improved oncolytic activity by introducing 2 copies of E2F promoter, E2F promoter DNA in pSP72-E2F cloning vector was excised by SalI/NheI and inserted into XhoI/BamHI site of the pΔE1sp1B-E2F cloning vector to prepare pΔE1sp1B-E2F-E2F vector. Rb7Δ19 DNA digested by EcoRI/BamHI was subcloned into EcoRI/BglII of the pΔE1sp1B-E2F-E2F vector to prepare pΔE1sp1B-E2F-E2F-Rb7Δ19 adenovirus E1 shuttle vector having E2F promoter 2 copies. The prepared pΔE1sp1B-E2F-E2F-Rb7Δ19 shuttle vector was subjected to homologous recombination to E1 region of dl324 Bst as an adenovirus total vector, thereby preparing an oncolytic adenovirus EE-Rd19.

In addition, in order to develop oncolytic adenovirus having better activity in hypoxic tumors, HRE 6 copies and E2F promoter were combined to prepare oncolytic adenovirus regulated replication by the combined promoter. First, to construct E1 adenovirus shuttle vector in which HRE 6 copies and E2F promoter were combined, and HRE 6 copies DNA obtained by digesting pSP 72-HRE6 with SalI/XhoI was inserted into XhoI site of pΔE1sp1A as an E1 shuttle vector, resulting in construction of pΔE1sp1A-HRE6 adenovirus E1 shuttle vector.

Rb7Δ19 DNA digested by EcoRI/BamHI was inserted into EcoRI/BglII site of the prepared pΔE1sp1A-HRE6 adenovirus E1 shuttle vector to prepare pΔE1sp1A-HRE6-Rb7Δ19. Finally, E2F DNA digested with NheI-EcoRV was subcloned into XbaI/EcoRV site of pΔE1sp1A-HRE6-Rb7Δ19 to prepare pΔE1sp1A-HRE6-E2F-Rb7Δ19 as E1 shuttle vector having promoter in which HRE 6 copies and E2F promoter were combined. The prepared pΔE1sp1A-HRE6-E2F-Rb7Δ19 adenovirus E1 shuttle vector was homologously recombinated to E1 region of dl324 Bst as adenovirus total vector to construct oncolytic adenovirus HE-Rd19.

Furthermore, we constructed improved oncolytic adenoviruses which have not only enhanced oncolytic activity but also enhanced activities in hypoxic tumors by combining E2F promoter 2 copies with HRE6. E2F promoter DNA in pSP72-E2F cloning vector was excised by SalI/NheI and was inserted into XhoI/BamHI position of the pΔE1sp1B-E2F cloning vector to prepare pΔE1sp1B-E2F-E2F vector. pΔE1sp1A-HRE6 digested by EcoRI-XbaI restriction enzyme and pΔE1sp1B-E2FE2F digested by EcoRI-NheI restriction enzyme were ligated to prepare pΔE1sp1B-HRE6-E2F-E2F. The E1 shuttle vector prepared as described above was homologously recombinated to E1 region of dl324 Bst as adenovirus total vector to construct oncolytic adenovirus HEE-Rd19.

Figure 1:
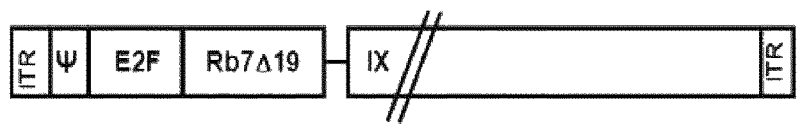
FIG. 1 represents diagram of oncolytic adenoviruses E-Rd19, EE-Rd19, HE-Rd19 and HEE-Rd19 in which the replication was regulated by transcription regulatory region combinated HRE6 copies and E2F promoter.
Figure 1:
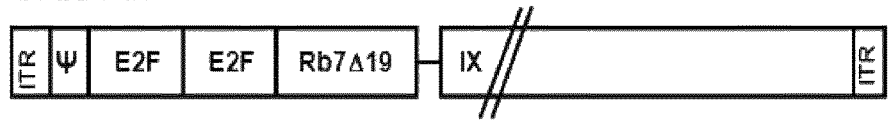
Figure 1:
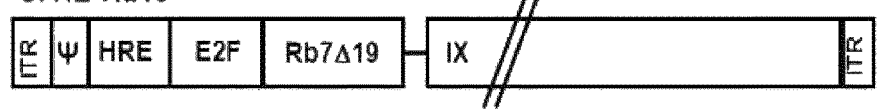
Figure 1:
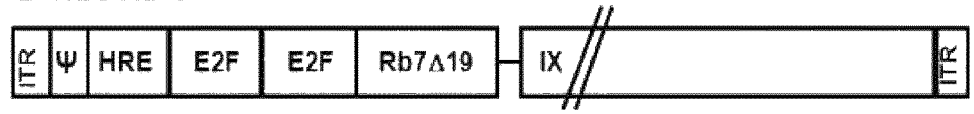
Figure 2A:
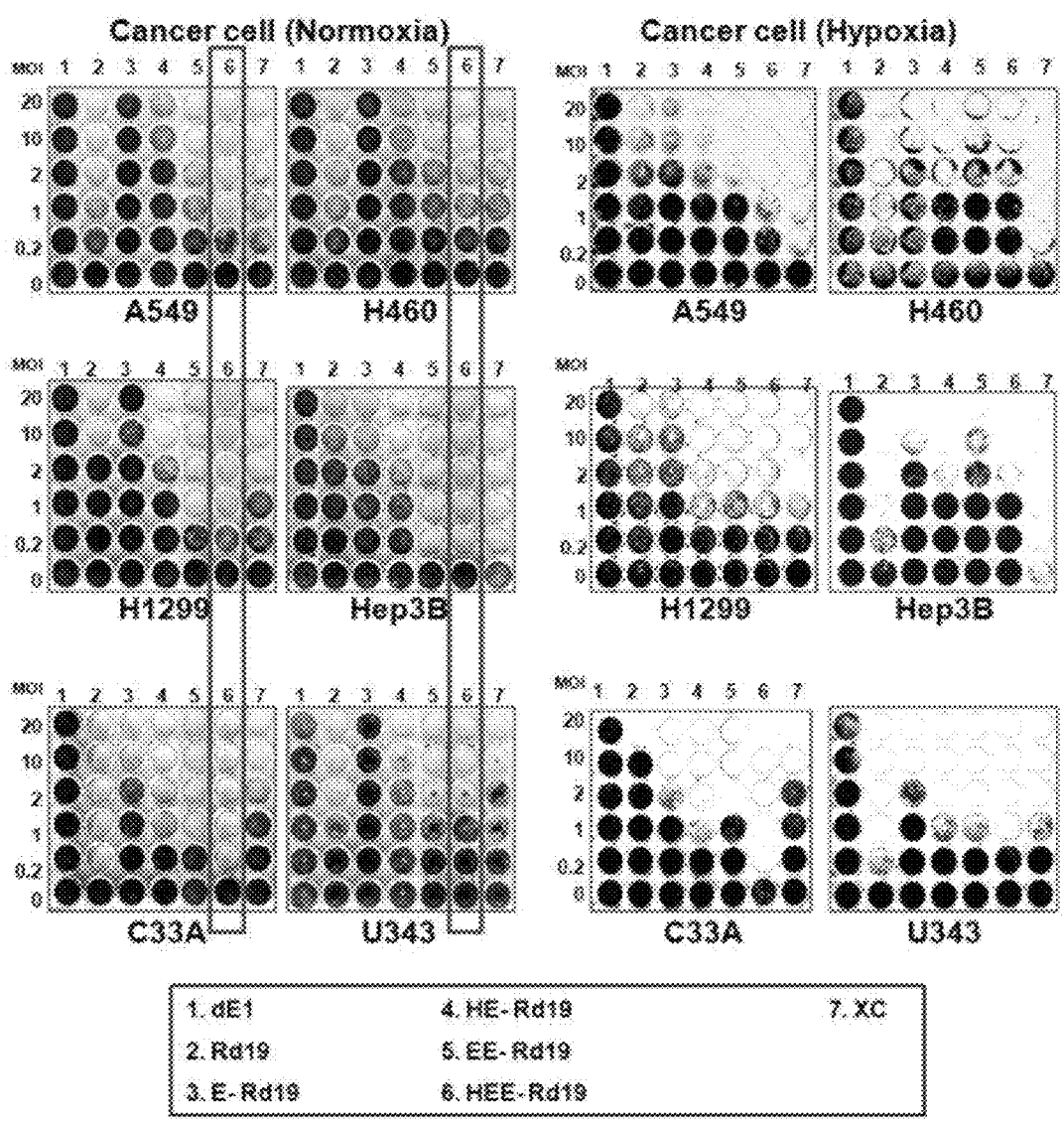
FIGS. 2a-b represents results of comparison on oncolytic activity of adenoviruses in which E3F promoter is recombinated.
Figure 2B:
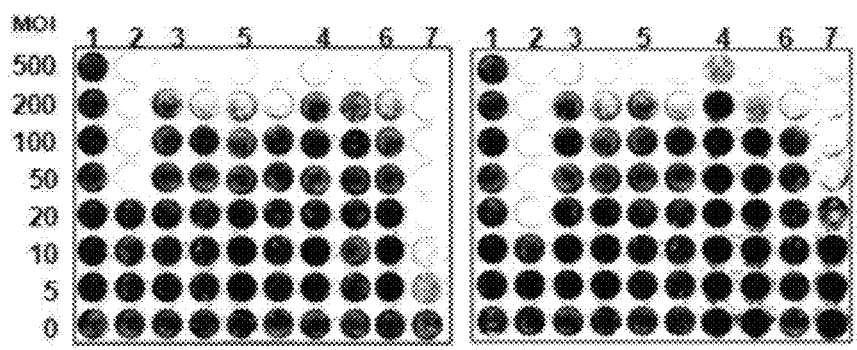
Figure 3:
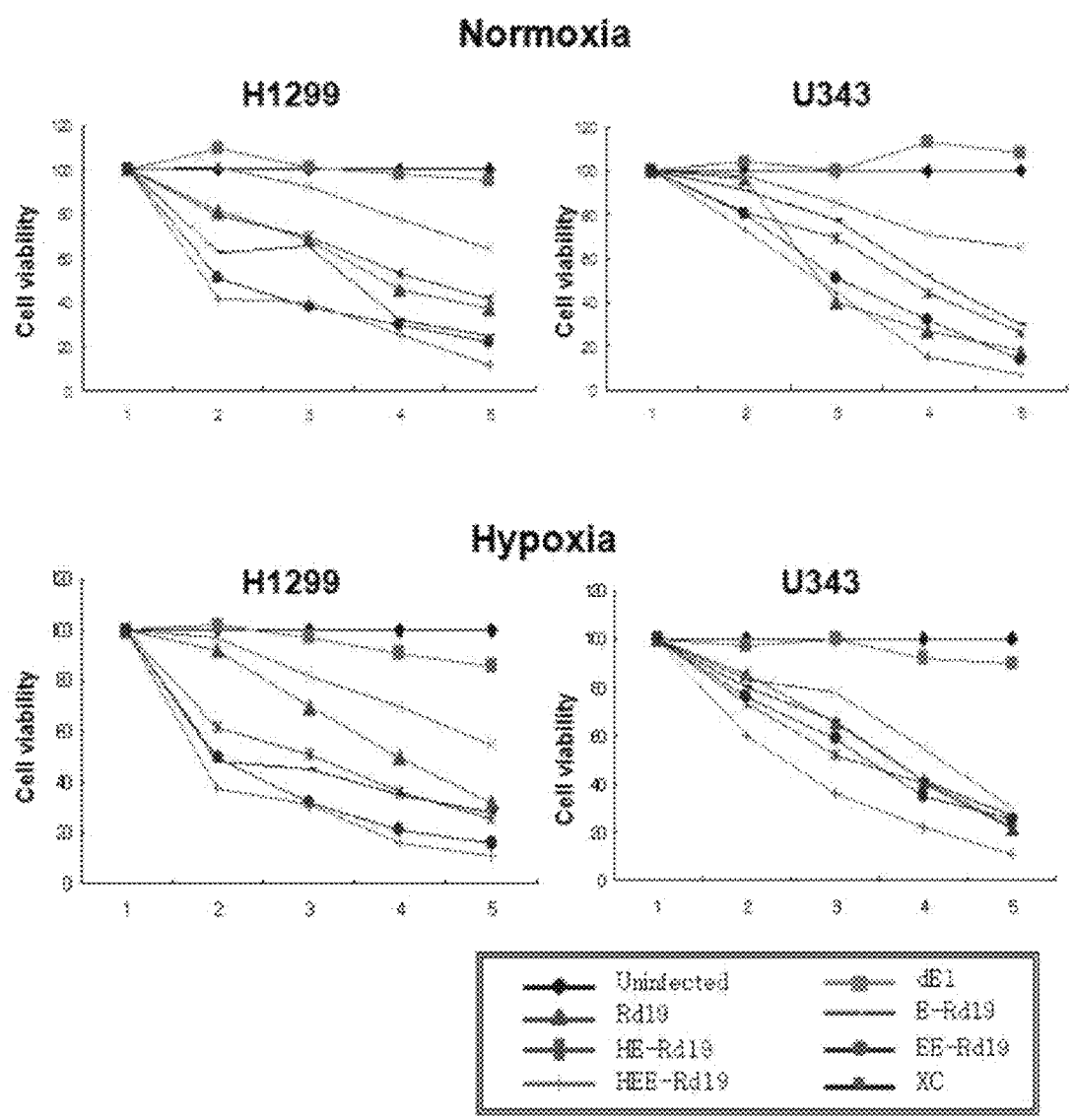
FIG. 3 represents MTT assay results of comparison on oncolytic activity of adenoviruses in which E3F promoter is recombinated.

Verification on Cytopathic Effect of Oncolytic Adenovirus Having E-Rd19, EE-Rd19, HE-Rd19 and HEE-Rd19 Promoter-MTT Assay To verify oncolytic activity (cytopathic effect) of E-Rd19, EE-Rd19, HE-Rd19 and HEE-Rd19 oncolytic adenovirus, several types of tumor cell lines and normal cell lines (e.g, BJ and MRC5) were infected by each virus with various concentration titers and the cytopathic effect was analyzed. As shown in FIG. 2, oncolytic adenovirus (HEE-Rd19) in which the replication was regulated by HRE-E2F-E2F promoter showed stronger the cytopathic effect than the oncolytic adenoviruses (E-Rd19, HE-Rd19, and EE-Rd19) regulated the replication by E2F, HRE-E2F or E2F-E2F. Particularly, oncolytic adenovirus (HEERd19) in which the replication was regulated by recombinant HREE2F-E2F promoter in all tumor cell lines used in the present invention showed similar the cytopathic effects with or stronger the cytopathic effects than the control group Rd19 or wild type adenovirus (XC), whereas normal cell lines showed lower the cytopathic effects than the wild type adenovirus. Therefore, it would be appreciated that the oncolytic adenovirus has an excellent tumor cell-specificity. MTT assay was conducted to quantify the cytopathic effect. As a result, oncolytic adenovirus (HEE-Rd19) in which the replication was regulated by recombinant HREE2F-E2F promoter showed similar the cytopathic effects with or stronger the cytopathic effects than the control group Ad-Rb7Δ19 or wild type adenovirus. Under the hypoxia condition, the cytopathic effect of HEE-Rd19 was more increased by HRE than that of the normal condition (FIG. 3). Similarly, under the hypoxia condition, the cytopathic effect of HE-Rd19 combinated with HRE6 was increased than that of E-Rd19. Therefore, it would be appreciated that HRE6 acts as an enhancer under the hypoxia condition.

Figure 4:
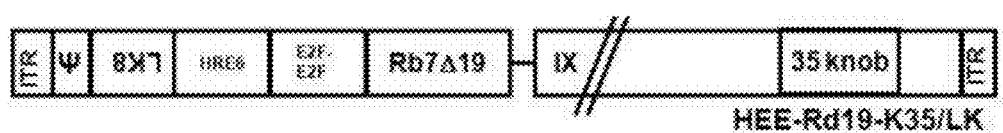
FIG. 4 represents diagram of LK8-expressing oncolytic adenovirus HEE-Rd19-K35/LK in which E2F promoter is recombinated.

Construction of LK8-Expressing Oncolytic Adenovirus in which E2F Promoter is Recombinated To prepare E1 shuttle vector having LK8 insertion which inhibits proliferation of vascular endothelial cells, the LK8 gene in pcDNA was digested by NheI/XhoI and inserted into pΔE1sp1A-HRE-E2F-E2F-Rb7Δ19 pre-incubated with NheI/SalI, giving pΔE1sp1A-LK8-HRE-E2F-E2F-Rb7Δ19 as an E1 adenovirus shuttle vector. E1 region of the adenovirus total vector of dl324-35K was digested by BstBI restriction enzyme and then was subject to homologous recombination with the LK8-expressing E1 shuttle vector pre-digested by XmnI to construct LK8-expressing oncolytic adenovirus HEE-Rd19-K35/LK (FIG. 4).

The adenovirus was proliferated in A549 cell line. Titers (plaque forming unit; PFU) were analyzed by limiting titration assay.

Figure 5:
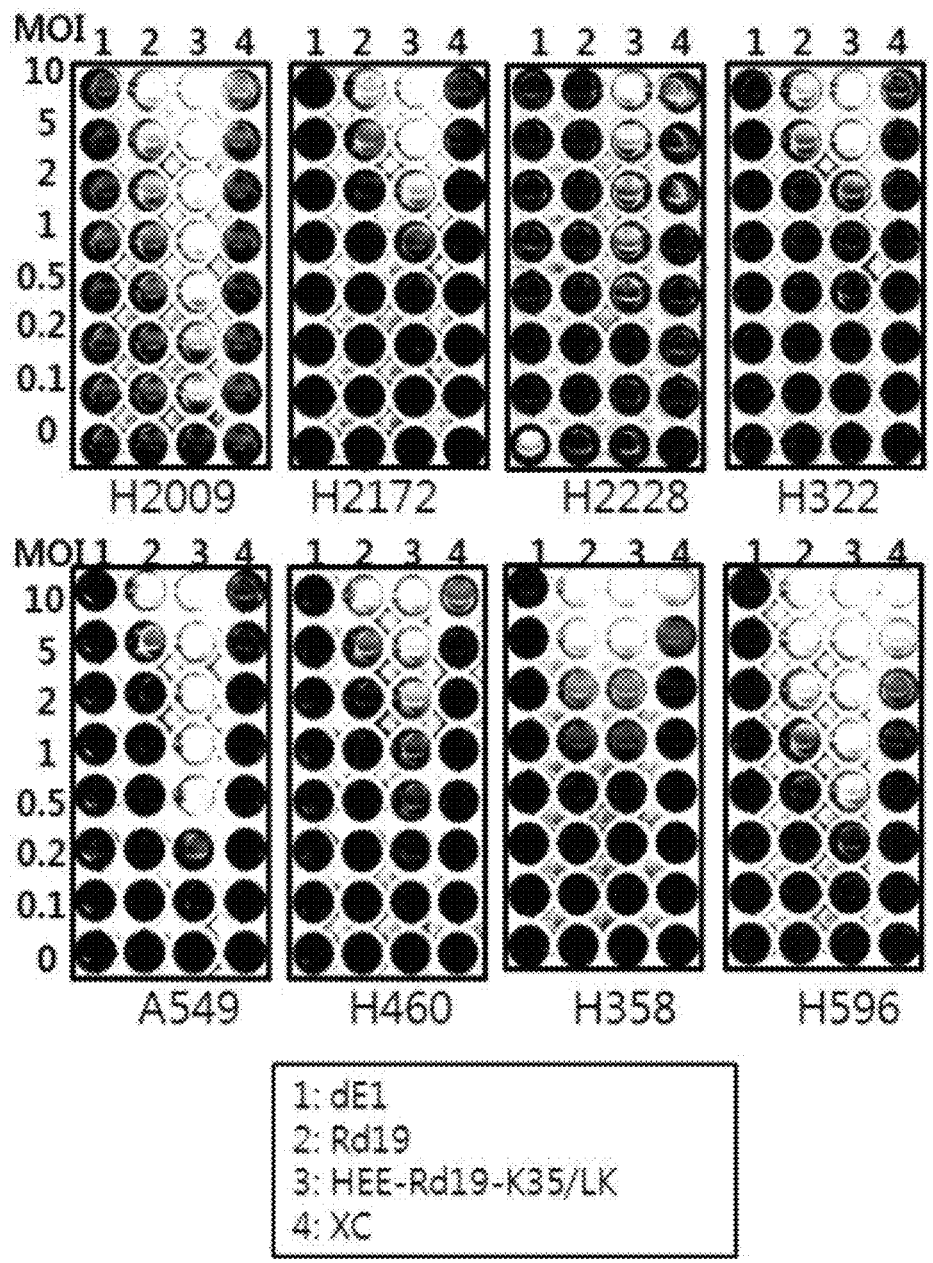
FIG. 5 represents results of oncolytic activity of LK8-expressing oncolytic adenovirus HEE-Rd19-K35/LK.
Figure 6:
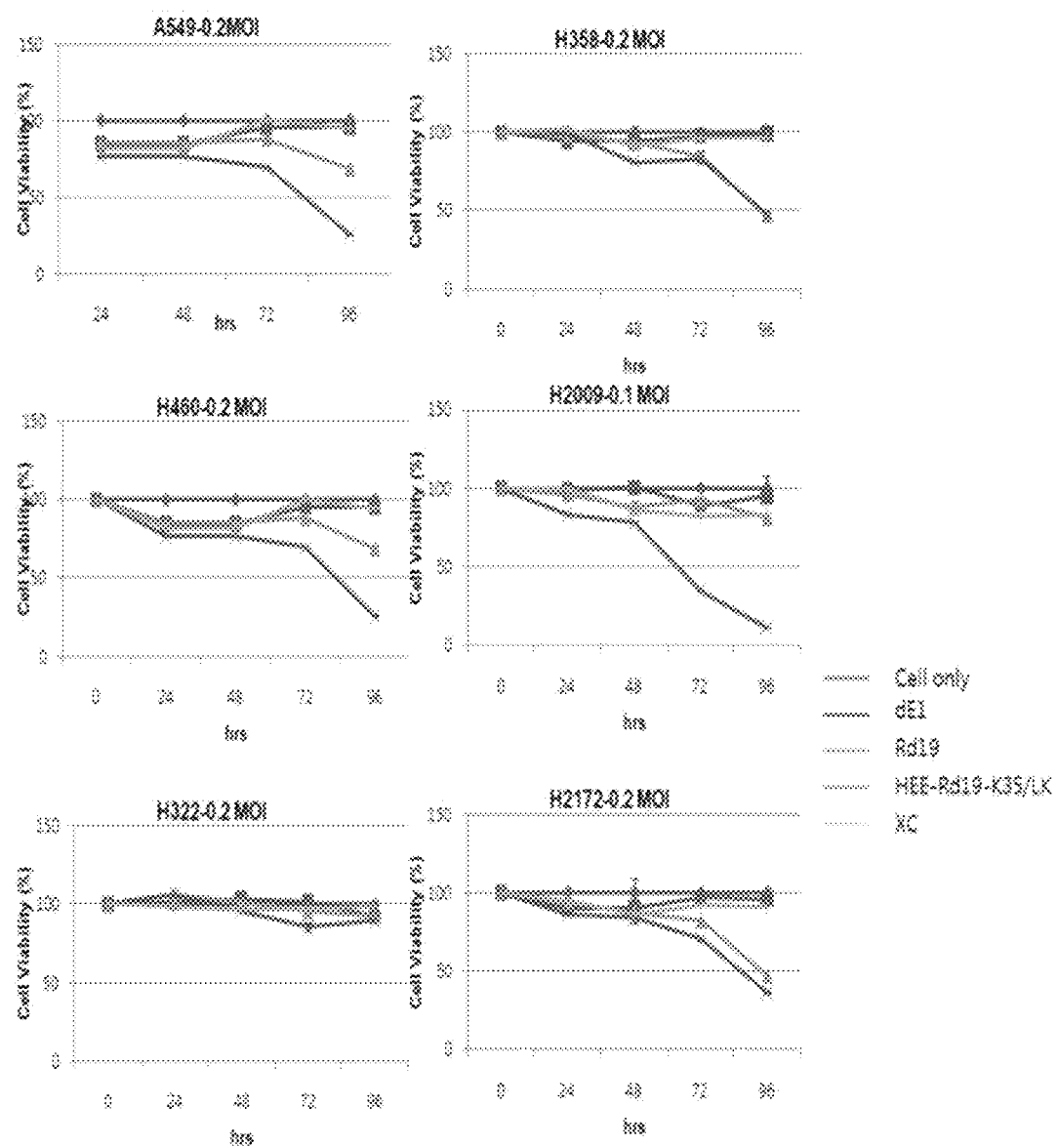
FIG. 6 represents MTT assay results of oncolytic activity of LK8-expressing oncolytic adenovirus HEE-Rd19-K35/LK.

Verification on Cytopathic Effect of LK8-Expressing Oncolytic Adenovirus HEE-Rd19-K35/LK in which E2F Promoter is Recombinated To verify oncolytic activity (cytopathic effect) of LK8-expressing oncolytic adenovirus HEE-Rd19-K35/LK in which E2F promoter is recombinated, several types of tumor cell lines were infected by each virus with various concentration titer and the cytopathic effect was analyzed (FIG. 5). As shown in FIG. 5, HEE-Rd19-K35/LK showed much stronger the cytopathic effect the control group Rd19 or wild type adenovirus XC. In addition, MTT assay was conducted to quantify the cytopathic effect of HEE-Rd19-K35/LK. Several types of lung cancer cell lines (A549, H358, H2009, H596, H2172 and HCC827) were infected by replication-incompetent adenovirus dE1 as negative control group, replication-competent adenovirus Rd19 as control group which was non-substituted with the fiber, and oncolytic adenovirus HEE-Rd19-K35/LK which was regulated the replication by modified E2F promoter and was substituted with the adenovirus type 35 fiber with 0.1-0.5 MOI, and the cell viability was hourly measured through MTT assay (FIG. 6). As shown in FIG. 6, the cytopathic effect of HEE-Rd19-K35/LK in all lung cancer cell lines used in the present invention was increased as compared with that of control group Rd19. Particularly, in H322 cell line, Rd19 as control group which was non-substituted with the fiber showed similar the viral replicative ability and the cytopathic effect with oncolytic adenovirus HEE-Rd19-K35/LK which was substituted with the adenovirus type 35 fiber. These results are correspond with the result that the expression level of CAR (Coxsackie and Adenovirus Receptor) as adenovirus cell receptor is high and the expression level of CD45 as receptor of type 35 fiber is low. In summary, the present oncolytic adenovirus HEE-Rd19-K35/LK which was regulated the replication by modified E2F promoter and was substituted with the adenovirus type 35 fiber was increased viral infection ability by the recombination of promoter and the substitution of fiber, whereby it is verified that the effective cytopathic effect was induced.

Figure 7:
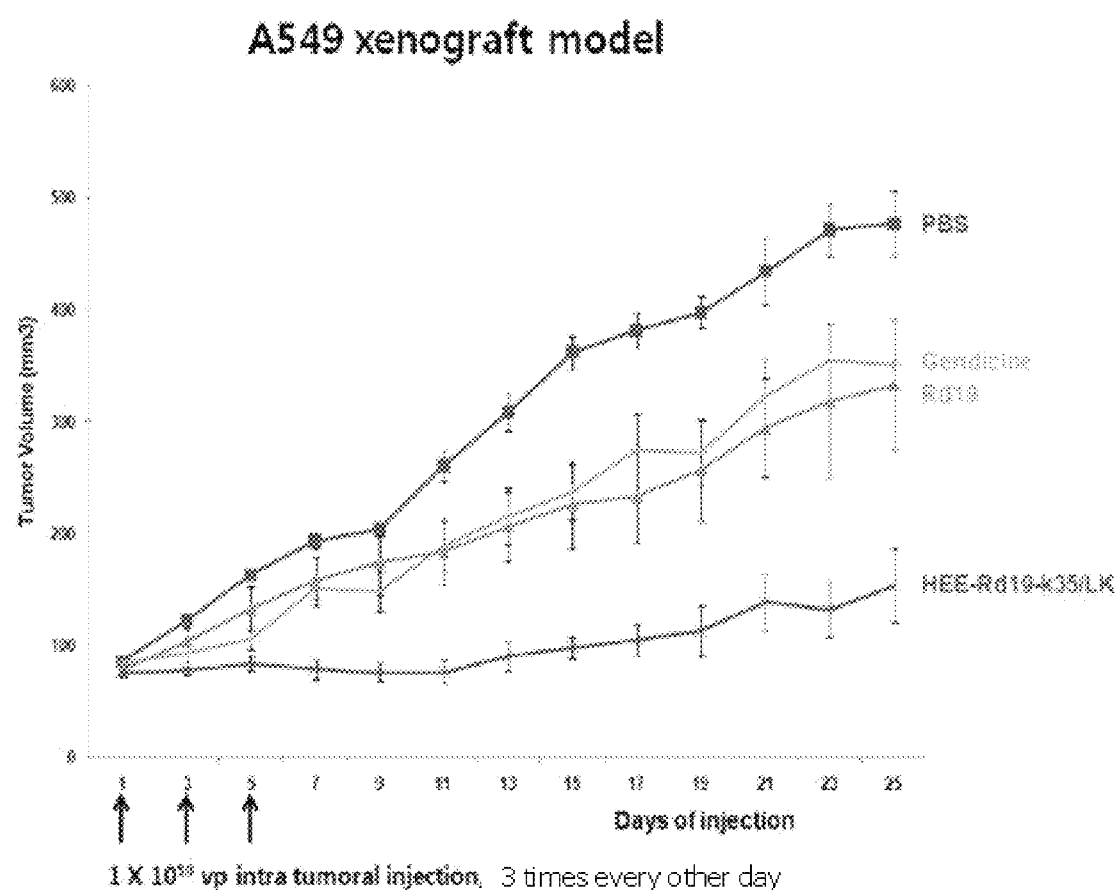
FIG. 7 represents results that in order to verify the in vivo antitumor effect of oncolytic adenovirus HEE-Rd19-K35/LK, human lung cancer cell line A549 was subcutaneously injected into the abdomen of nude mice, the tumor was formed, 1×1010 VP of Rd19 or HEE-Rd19-K35/LK adenovirus was administered intratumorally 3 times every other day and tumor growth was observed. PBS-administered group was used as negative control.

Verification on Antitumor Effect of LK8-Expressing Oncolytic Adenovirus HEE-Rd19-K35/LK in which E2F Promoter is Recombinated To verify the in vivo antitumor effect of oncolytic adenovirus HEE-Rd19-K35/LK, human lung cancer cell line A549 was subcutaneously injected into the abdomen of nude mice. When the tumor was formed, $1\times10^{10}$ VP of Rd19 or HEE-Rd19-K35/LK adenovirus was administered intratumorally 3 times every other day and tumor growth was observed. PBS-administered group was used as negative control (FIG. 7). The tumor volume increased abruptly to approximately 500 mm$^3$ on day 25 post-treatment in the nude mice treated with the negative control group PBS, whereas the tumor growth was substantially delayed when Rd19 or HEE-Rd19-K35/LK was administered. i.e., the mice administered with Rd19 or HEE-Rd19-K35/LK showed significantly decreased tumor volume of approximately 300 mm$^3$ (by 60%) or 100 mm$^3$ (by 20%), respectively, on day 25 post-treatment as compared with control group. In addition, where the mice were administered with the commercialized gene therapeutic agent Gendicine, the tumor volume was approximately 350 mm$^3$ on day 25 post-treatment. Therefore, it would be appreciated that HEE-Rd19-K35/LK has the excellent antitumor effect as compared with Gendicine.

Construction of Replication-Incompetent Adenovirus in which E2F and TERT Promoter were Recombinated (HRE6-TERT-E2F or HRE6-E2F-TERT)

To verify the replicating ability difference of adenovirus by promoter, the promoter was combined with HRE6 copies, modified TERT promoter and E2F promoter. First, replication-incompetent adenovirus was constructed. Its GFP expression is regulated by the promoter in which HRE 6 copies, modified TERT promoter and E2F promoter were recombinated in order HRE6/TERT/E2F. E2F promoter in pSP72-E2F vector was excised by ClaI and SalI restriction enzymes and cloned into SfuI, SalI site of the pSP72-mTERT prepared previously by the present inventors to prepare pSP72-TERT-E2F. HRE 6 copies in pGL3-HRE6-APF vector were excised by ClaI restriction enzyme and then cloned into ClaI site to prepare pSP72-HRE6/TERT/E2F. Afterwards, the recombinant promoter HRE6/TERT/E2F in pSP72-HRE6/TERT/E2F was excised by SalI and EcoRI and then cloned into the E1 adenovirus shuttle vector pΔE1sp1B(ψ) digested by XhoI and EcoRI to prepare pΔE1sp1B(ψ)-HRE6/E2F/TERT.

The pΔE1sp1B(ω)-HRE6/E2F/TERT digested by EcoRI and XbaI, and cloned with EGFP which is obtained by digesting pCDNA3.1/zeo-EGFP with EcoRI, NheI to prepare pΔE1sp1B(ψ)-HRE6/TERT/E2F-EGFP.

In addition, in order to construct replication-incompetent adenovirus in which GFP expression was regulated by promoter recombinated in order HRE6/E2F/TERT, E2F-TERT obtained by digesting pΔE1sp1B(ψ)-E2FTERT-Rb7Δ19, which is prepared previously by the present inventors, with EcoRI and ClaI was inserted into EcoRI and ClaI site of E1 shuttle vector pΔE1sp1B(ψ) to prepare pΔE1sp1B(ψ)-E2F-TERT. HRE6 digested by ClaI in pGL3-HRE6-APF vector was cloned into ClaI site of pΔE1sp1B(ψ)-E2F-TERT to prepare pΔE1sp1B(ψ)-HRE6/E2F/TERT. Afterwards, EGFP which is obtained by digesting pCDNA3.1/zeo-EGFP with EcoRI and NheI was inserted into pΔE1sp1B(ψ)-HRE6/E2F/TERT digested by EcoRI and XbaI to prepare pΔE1sp1B(ψ)-HRE6/E2F/TERT-EGFP shuttle vector.

Figure 8:
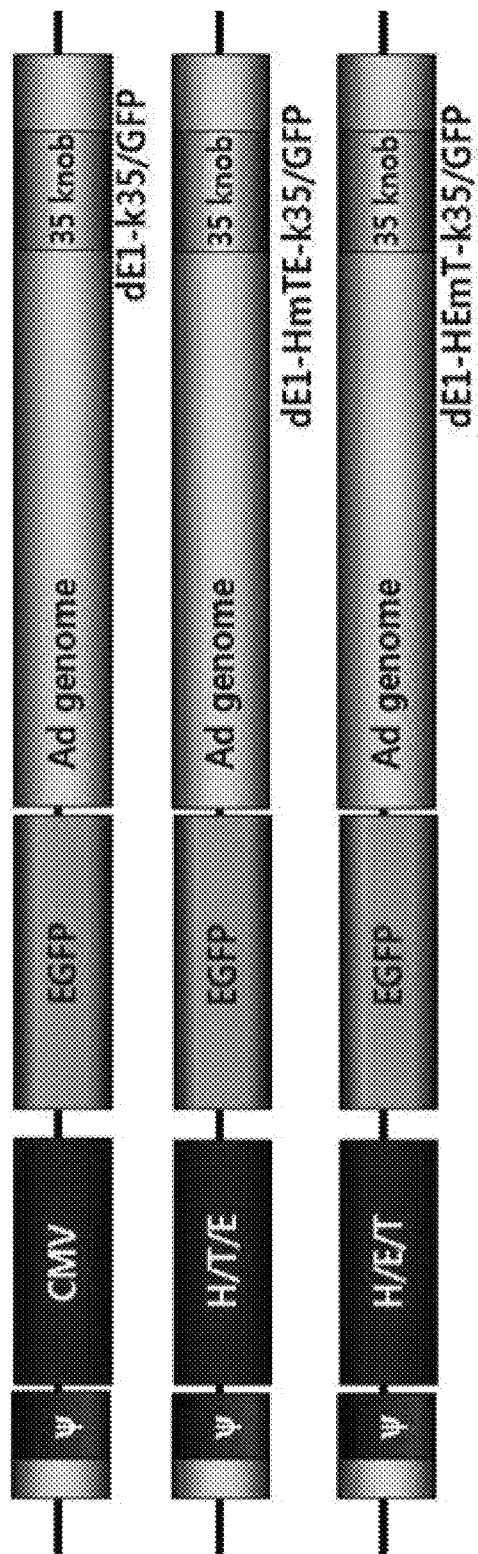
FIG. 8 represents diagram of replication-incompetent adenoviruses dE1-HmTE-k35/GFP and dE1-HEmT-k35/GFP in which GFP expression was regulated by promoter recombinated with HRE6, E2F and TERT promoter.

The prepared pΔE1sp1B(ψ)-HRE6/TERT/E2F-EGFP or the prepared pΔE1sp1B(ψ)-HRE6/E2F/TERT-EGFP adenovirus E1 shuttle vector was homologously recombinated into E1 region of adenovirus total vector dE1-k35 to construct dE1-HmTE-k35/GFP and dE1-HEmTk35/GFP adenovirus (FIG. 8).

Figure 9B:
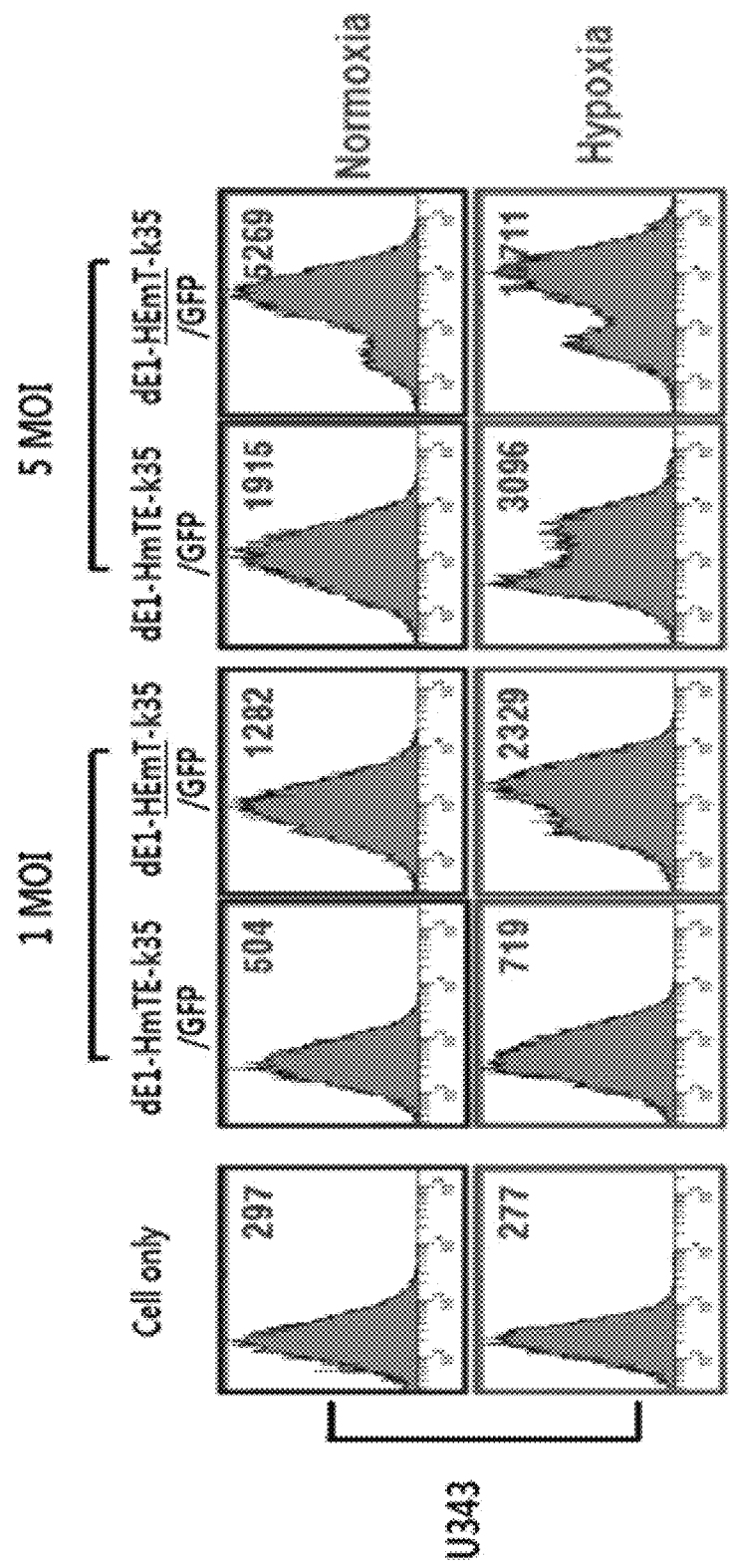
Figure 10:
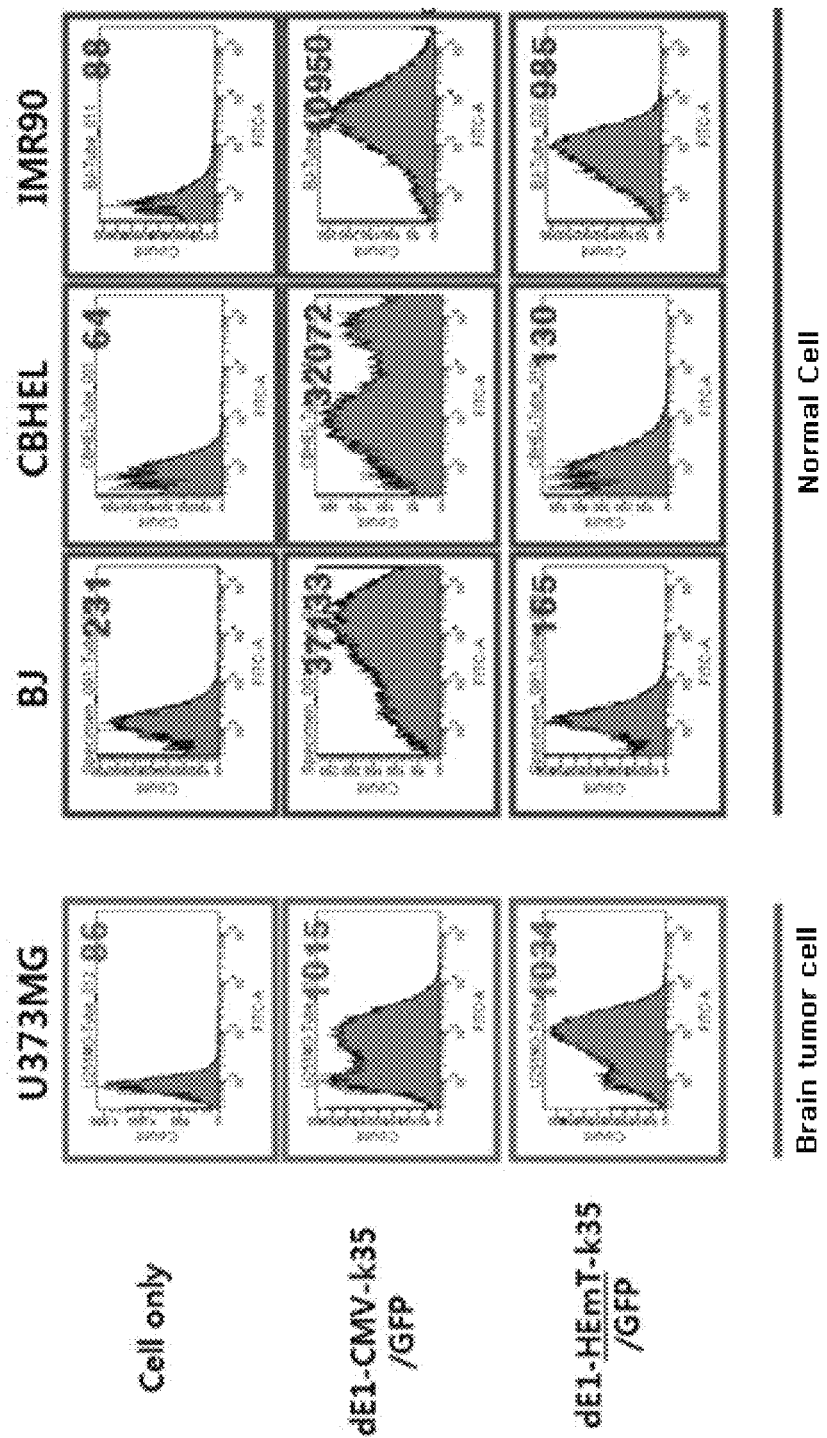
FIG. 10 represents results of comparison on GFP expression level by CMV promoter or HEmT recombinant promoter.
Figure 11:
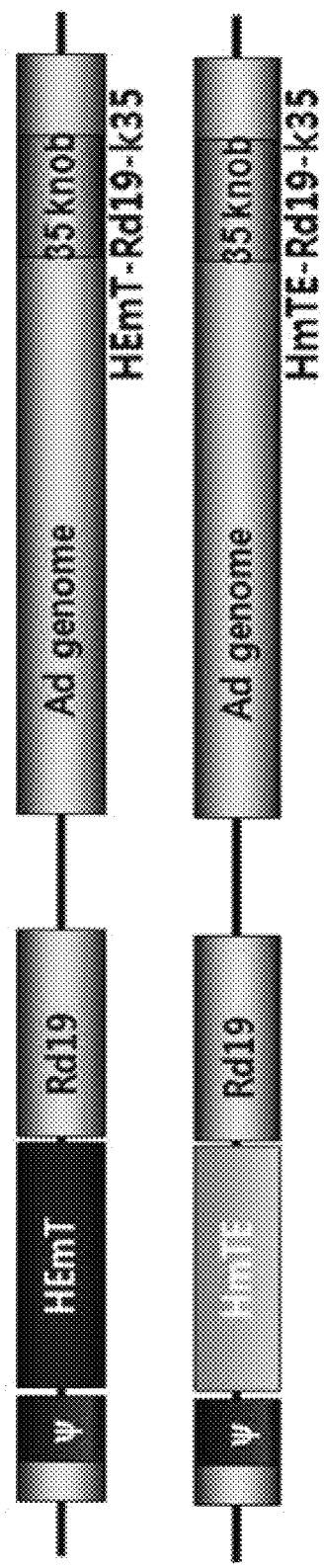
FIG. 11 represents diagram of oncolytic adenoviruses HEmT-Rd19-k35 and HmTE-Rd19-k35 in which the replication was regulated by promoter recombinated with HRE6 copies, E2F and TERT promoter.

Comparison on Gene Delivery Efficiency of dE1-HmTE-k35/GFP and dE1-HEmT-k35/GFP Adenovirus For comparison of activities of the prepared recombinant promoters, several types of tumor cells were infected by the prepared replication-incompetent adenoviruses. After 36 hours, the GFP expression was verified using FACS (FIG. 9). As shown in FIG. 9, the GFP expression of the hypoxia condition was significantly increased by dE1-HEmT-k35/GFP and dE1-HmTE-k35/GFP virus in which HRE enhancer is inserted, as compared with that of the normal condition. This result means that HRE acts as the enhancer to increase gene delivery efficiency of viruses (dE1-HEmT-k35/GFP and dE1-HmTE-k35/GFP) under hypoxia condition. In the brain tumor cell line U343 and other tumor cell lines (Hep1, MDA MB231), the gene delivery efficiency by dE1-HEmTk35/GFP and dE1-HmTE-k35/GFP was excellent. Particularly, the GFP expression in cells infected by dE1-HEmT-k35/GFP was significantly increased as compared with that of dE1-HmTE-k35/GFP. Through these results, it would be appreciated that HEmT recombinant promoter activity in tumor cells was significantly increased as compared with that of HmTE recombinant promoter activity. As shown in FIG. 10, the GFP expression regulated by CMV promoter in dE1-CMV-k35/GFP showed high level in tumor cell line U373MG and normal cell lines BJ, CBHEL and IMR90. In contrast, the GFP expression by dE1-HEmT-k35/GFP only in tumor cell line U373MG was similar level with that of dE1-CMV-k35/GFP. Therefore, it would be appreciated that the promoter activity was very high. In addition, the GFP expression by dE1-HEmT-k35/GFP in normal cell lines was similar level with that of the negative control group. Therefore, it would be appreciated that the specificity for tumor cells of the HEmT promoter was very high.

Construction of Oncolytic Adenovirus HEmTRd19-k35 and HmTE-Rd19-k35 Regulated by Promoter in which HRE6 Copies, E2F Promoter and Modified TERT Promoter Were Recombinated To construct oncolytic adenovirus HEmT-Rd19-k35 regulated by promoter in which HRE6 copies, E2F promoter and modified TERT promoter were combined in order, E2F promoter in pSP72-E2F vector was excised by ClaI and SalI and inserted into adenovirus E1 shuttle vector pΔE1sp1B (ψ)-Rb7Δ19, which had been previously prepared by the present inventors, digested by ClaI and SalI to prepare pΔE1sp1B(ψ)-Rb7Δ19-E2F. The pΔE1sp1B(ψ)-Rb7Δ19-E2F was digested by EcoRI and XhoI, cloned with modified TERT which was obtained by digesting pcDNA3.1-mTERT with EcoRI and XhoI, and cloned with E2F promoter which was excised by ClaI and SalI in pSP72-E2F vector to prepare pΔE1sp1B(ψ)-Rb7Δ19-E2F-TERT. Finally, HRE6 copies in pGL3-HRE6-APF vector were excised by ClaI restriction enzyme and cloned into ClaI site of pΔE1sp1B(ψ)-Rb7Δ19-E2F-TERT to prepare pΔE1sp1B(ψ)-Rb7Δ19-HRE6/E2F/mTERT as adenovirus E1 shuttle vector.

Meanwhile, in order to construct oncolytic adenovirus HmTE-Rd19-k35 regulated by promoter in which HRE6 copies, modified TERT promoter, and E2F promoter were combined in order HRE6/TERT/E2F, first, E2F promoter in pSP72-E2F vector was excised by EcoRV and HindIII and inserted into adenovirus E1 shuttle vector pΔE1sp1A(ψ), which is previously prepared by the present inventors, digested by EcoRV and HindIII to prepare pΔE1sp1A(ψ)-E2F.

E1 shuttle vector pΔE1sp1B(ψ) was digested by EcoRI and XhoI, cloned with TERT which is obtained by digesting pcDNA3.1-mTERT with EcoRI and XhoI to prepare pΔE1sp1B(ψ)-TERT. Modified TERT which is obtained by digesting ΔE1sp1B(ψ)-TERT with ClaI and EcoRV was inserted into ClaI and EcoRV site of pΔE1sp1A(ψ)-E2F to prepare pΔE1sp1A(ψ)-TERT-E2F. The prepared pΔE1sp1A (ψ)-TERT-E2F was digested by ClaI and SalI and inserted into ClaI and SalI site of E1 shuttle vector pΔE1sp1B(ψ)-Rb7Δ19, which is previously prepared by the present inventors, to prepare pΔE1sp1B(ψ)-Rb7Δ19-TERT-E2F. Finally, HRE6 in pGL3-HRE6-APF vector was excised by ClaI restriction enzyme and cloned into ClaI site of pΔE1sp1B (ψ)-Rb7Δ19-TERT-E2F to prepare ΔE1sp1B(ψ)-Rb7Δ19-HRE6/TERT/E2F as adenovirus E1 shuttle vector. The prepared adenovirus E1 shuttle vectors pΔE1sp1B(ψ)-Rb7Δ19-HRE6/TERT/E2F and pΔE1sp1B(ψ)-Rb7Δ19-HRE6/TERT/E2F were homologously recombinated into E1 region of adenovirus total vector dl324-35K to construct HEmTRd19-k35 and HmTE-Rd19-k35 as oncolytic adenoviruses in which the viral replication was regulated by the recombinant promoter.

Construction of Oncolytic Adenovirus HEmT-Rd19-k35/DCN the Replication of which is Regulated by HEmT Promoter and Expresses the Decorin Gene Capable of Disintegrating Extracellular Matrix Decorin is a protein belongs to the class of SLRP (small leucin rich proteoglycan), consisting of 10-12 leucin rich repeats. Its core region forms an arch such that various growth factors or Decorin receptor in extracellular matrix are easily binded. It is known that Decorin inhibits the activity of TGF (tumor growth factor)-β to protect collagen fibrosis, is involved in matrix assembly and inhibits tumor cell growth to act natural antagonist in tumor formation and growth. In addition, Decorin reacts with components of the extracellular matrix such as growth factors or metal ions to stimulate various MMP expressions such as MMP-1, resulting in degradation of the extracellular matrix. Recent research has been reported that where several types of Decorin as novel biological ligand for EGFR (epidermal growth factor receptor) were treated, EGFR function was inactivated by binding of Decorin with EGFR to stimulate the expression of endogenous cyclin dependent) $p21^{WAF1}$, whereby resulting in cell killing according to cell cycle G1 arrest induction. Therefore, as increasing the spread of the virus, Decorin-expressing adenovirus may not only increase the therapeutic gene of gene delivery efficiency, but also induce the tumor-specific killing effect by Decorin per se.

Based on these facts, in order to construct adenovirus expressing Decorin at E1 region of adenovirus, the digested Decorin DNA was subcloned into BamHI site of pCA14 cloning vector to prepare pCA14-Decorin. DCN expression cassette was obtained by incubating pCA14/DCNG plasmid with BglII restriction enzyme, and cloned into pΔE1sp1B (ψ)-Rb7Δ19, which had been previously prepared by the present inventors, by incubating with BamHI restriction enzyme to prepare pΔE1sp1B(ψ)-Rb7Δ19-DCN.

Figure 12:
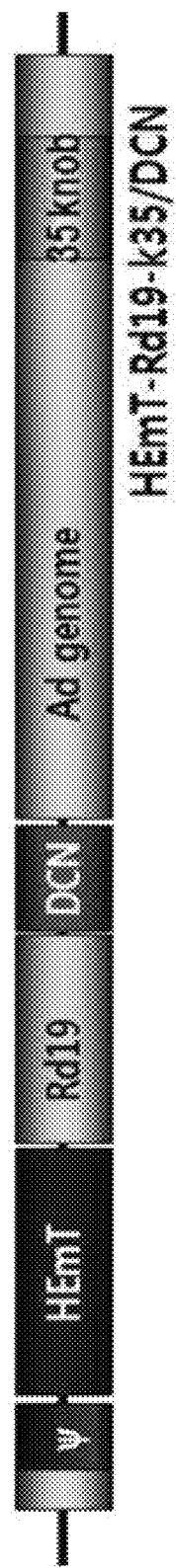
FIG. 12 represents diagram of decorin-expressing oncolytic adenovirus HEmT-Rd19-k35/DCN in which the replication was regulated by HEmT promoter.

Meanwhile, in order to cloning promoter, E2F-TERT was obtained by treating pΔE1sp1B(ψ)-E2F-TERT with ClaI and EcoRI restriction enzyme and cloned into pΔE1sp1B (ψ)-Rb7Δ19-DCNG shuttle vector to prepare pΔE1sp1B (ψ)-E2F-mTERT-Rb7Δ19-DCN. HRE6 copies were obtained by treating PGL3-HRE6-AFP plasmid with ClaI restriction enzyme and cloned into pΔE1sp1B(ψ)-E2F-mTERT-Rb7Δ19-DCN plasmid with ClaI restriction enzyme to prepare pΔE1sp1B(ψ)-HRE6/E2F/TERT-Rb7Δ19-DCN adenovirus shuttle vector. The prepared adenovirus shuttle vector was linearized using XmnI, and homologously recombinated with total vector dE1-k35 to construct HEmT-Rd19-k35/DCN virus. Afterwards, the prepared adenovirus was proliferated in A547 cell line. The viral titers were analyzed by limiting titration assay using (FIG. 12).

Construction of Oncolytic Adenovirus HEmT-Rd19-k35/CDTK(E3) and HEmT-Rd19-k35/DCN/CDTK Having HEmT Recombinant Promoter Insertion and Expressing the Decorin and CDTK Genes in E1 and E3 Region, Respectively.

HSV-TK (Herpes simplex virus-thymidine kinase) is the most commonly used drug sensitivity gene. It is therapeutic gene in antitumor that HSV-TK phosphorylates non-toxic prodrug ganciclovir (GCV) to inhibit DNA synthesis of infected cells, whereby dividing cells can be selectively killed. Thymidine kinase (TK) is an enzyme used for DNA synthesis in salvage pathway. HSV-TK is thymidine and nucleotide analogues and can phosphorylate ganciclovir used as an antiviral agent. Phosphorylated ganciclovir-triphosphate is inserted into DNA strand during DNA synthesis to disrupt the formation of DNA strand, finally resulting in inhibition of DNA synthesis. In addition, living tumor cells phagocyte dead tumor cells such that non-inserted-HSV-TK tumor cells are obtained ganciclovir-triphosphate and occur cell death to be induce bystander effect. The bystander effect also can be occurred by inducing tumor cell-specific immune response due to tumor cell killing. In addition, CD (cytosine deaminase) converts non-toxic 5-FC (5-fluorocytosine) to 5-FU (5-fluorouracil) having strong cytotoxicity and radiosensitivity. Recently, tumor-specific killing effect (cytopathic effect) by the CD gene expression has been reported in gene therapy using the CD gene. Based on this fact, the present inventors constructed oncolytic adenoviruses which express the decorin gene in E1 region and the CD and TK genes in E3 region of adenovirus the replication of which was regulated by the HEmT recombinant promoter having excellent tumor cell-specific activity.

Figure 13:
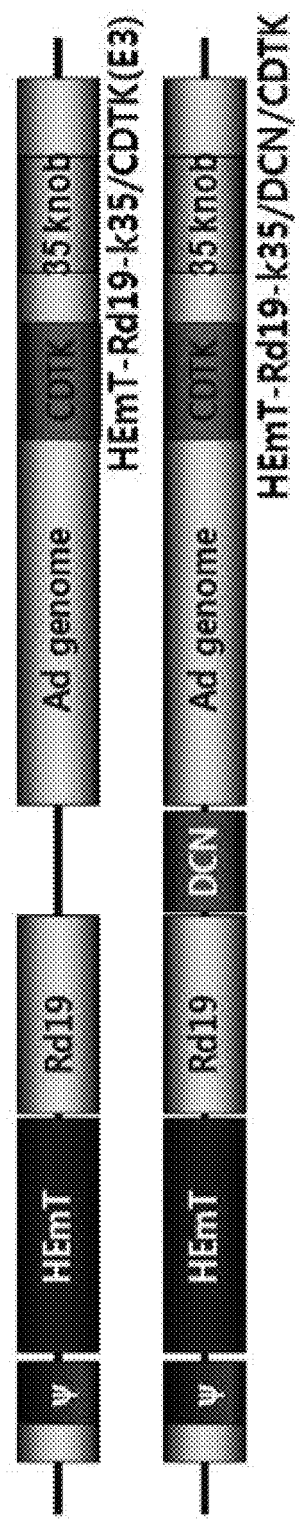
FIG. 13 represents diagram of decorin/CDTK-expressing oncolytic adenovirus.

To prepare CD and TK-expressing adenovirus E3 shuttle vector, human type CD-IRES-TK was obtained by incubating pCKhTK-IRES-hCD plasmid with BamHI restriction enzyme and inserted into pSP72/E3/CMV-PolA vector, thereby preparing pSP72-E3/CMV-CD-IRES-TK-PolA adenovirus E3 shuttle vector. The prepared vector was linearized using PvuI, and subject to homologous recombination with the prepared HEmT-Rd19-k35 and HEmT-Rd19-k35/DCN total vectors in E3 region to construct HEmT-Rd19-k35/CDTK(E3) and HEmT-Rd19-k35/DCN/CDTK virus, respectively (FIG. 13).

Verification on Decorin Expression of Oncolytic Adenovirus HEmT-Rd19-k35/DCN (Western Blot Assay)

Figure 14:
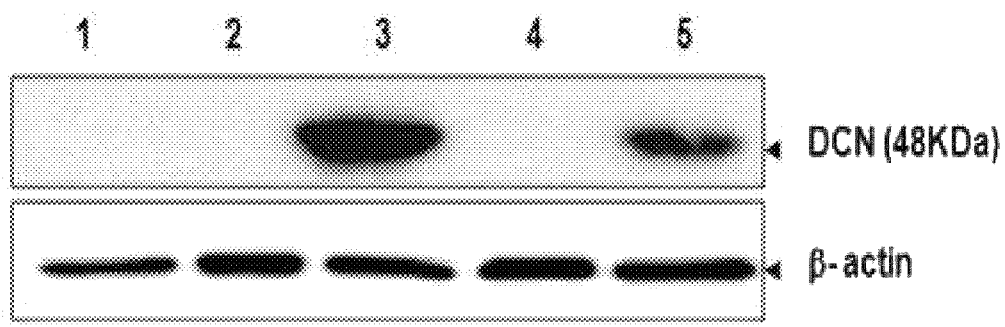
FIG. 14 represents verification results of decorin expression by HEmT-Rd19-k35/DCN oncolytic adenovirus.

To identify whether oncolytic adenovirus HEmT-Rd19-k35/DCN expresses sufficiently Decorin, western blotting was conducted. As shown in FIG. 14, it would be appreciated that Decorin was normally expressed by Rd19-k35/DCN and HEmTRd19-k35/DCN adenovirus used in the present invention.

Verification on Cytopathic Effect of Oncolytic Adenovirus in which the Replication was Regulated by HEmT Recombinant Promoter and Decorin was Expressed (CPE Assay)

Figure 15:
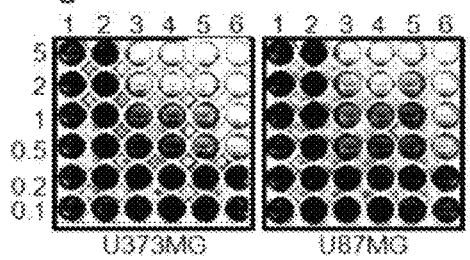
FIG. 15 represents comparison verification results of oncolytic activity of HEmT-Rd19-K35/DCN oncolytic adenovirus, c is bran tumor cell line infected by adenovirus, b is head and neck tumor cell line infected by adenovirus, c is other tumor cell line infected by adenovirus, and d is normal cell line by adenovirus.
Figure 15:
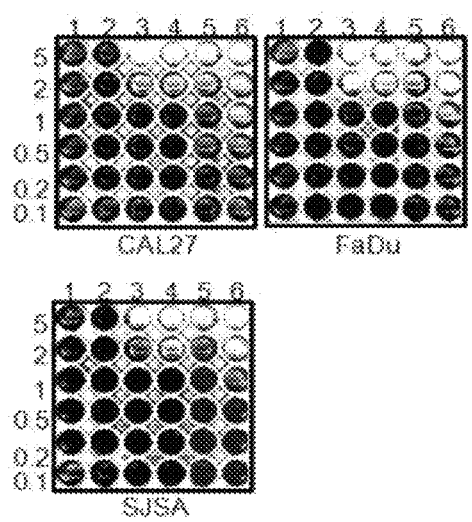
Figure 15:
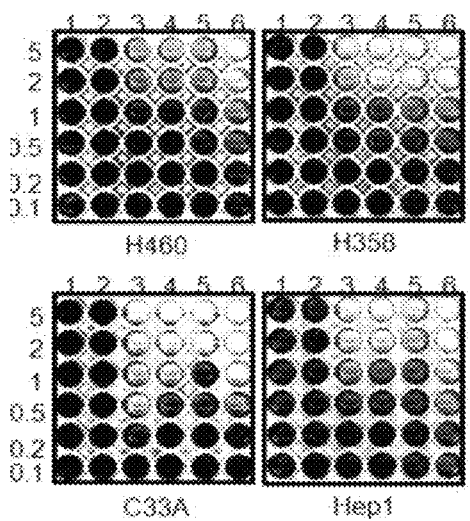
Figure 15:
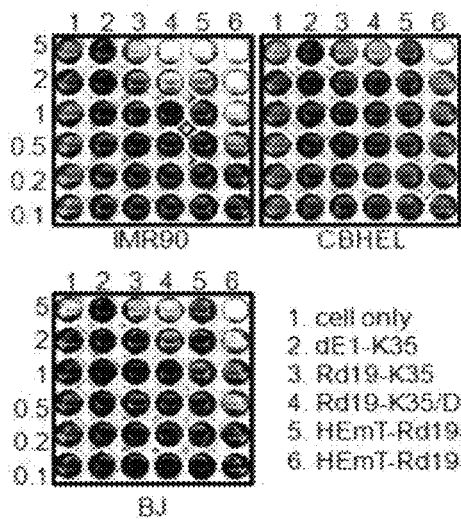

To verify oncolytic activity (cytopathic effect) of HEmT-Rd19-K35/DCN oncolytic adenovirus as prepared above, brain tumor cell lines (U373MG, U87MG, T98G, U343), head and neck tumor cell lines (CAL27, IMR90, SJSA), other tumor cell lines (H460, H358, C33A, Hep1) and normal cell lines (IMR90, BJ, CBHEL) were infected by each virus with various concentration titers and the cytopathic effect was analyzed (FIG. 15). As shown in FIG. 15, the cytopathic effect of Decorin-expressing oncolytic adenovirus Rd19-K35/DCN or HEmT-Rd19-K35/DCN was increased than that of the control group Rd19-K35 or HEmT-Rd19-K35, respectively. Therefore, it would be appreciated that the cytopathic effect of oncolytic adenovirus was increased by Decorin expression.

Verification on Cytopathic Effect of Oncolytic Adenovirus HEmT-Rd19-K35/DCN (MTT Assay)

Figure 16A:
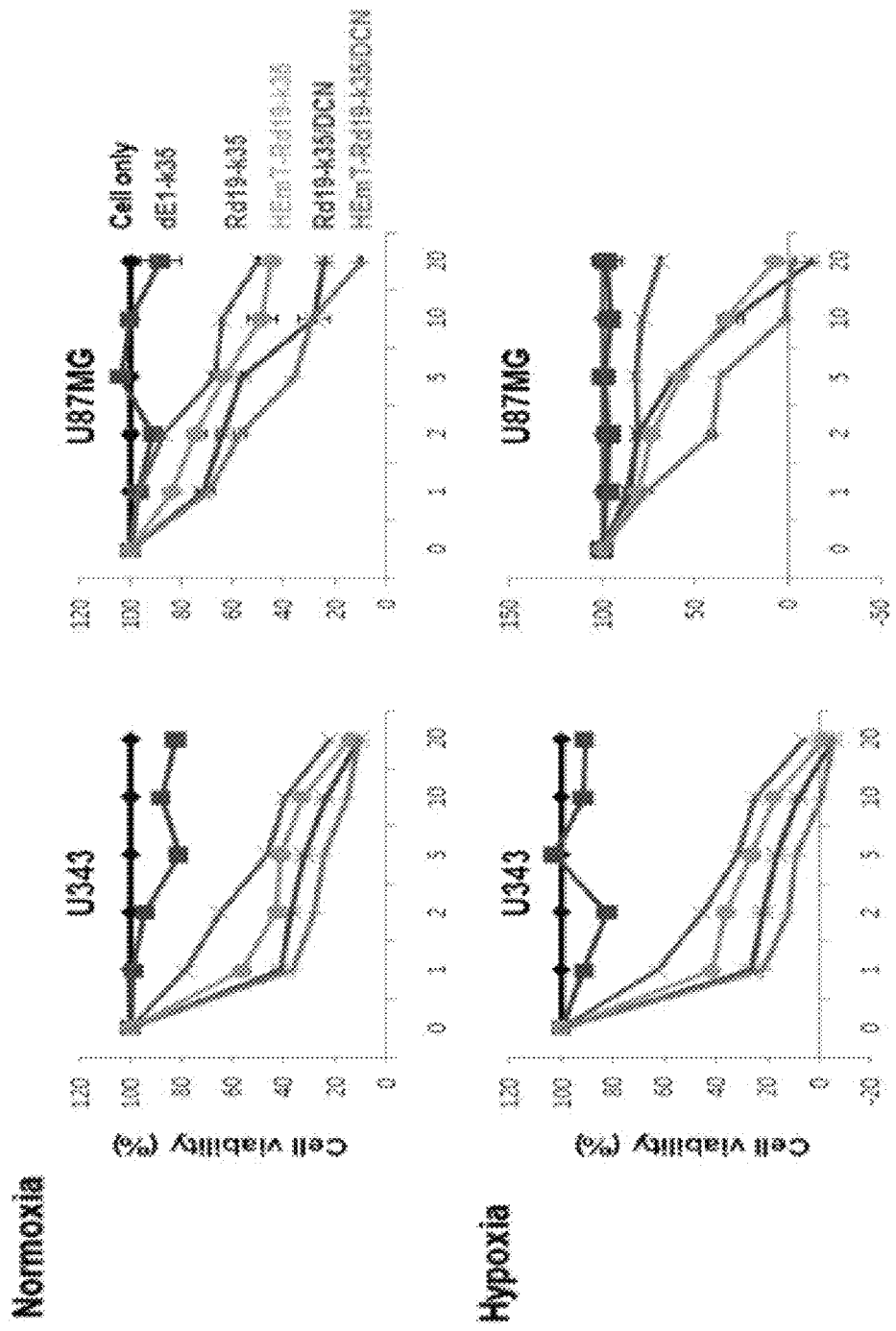
FIG. 16 represents comparison verification results of oncolytic activity of decorin-expressing oncolytic activity of Rd19-k35/DCN and HEmT-Rd19-k35/DCN oncolytic adenoviruses.
Figure 16B:
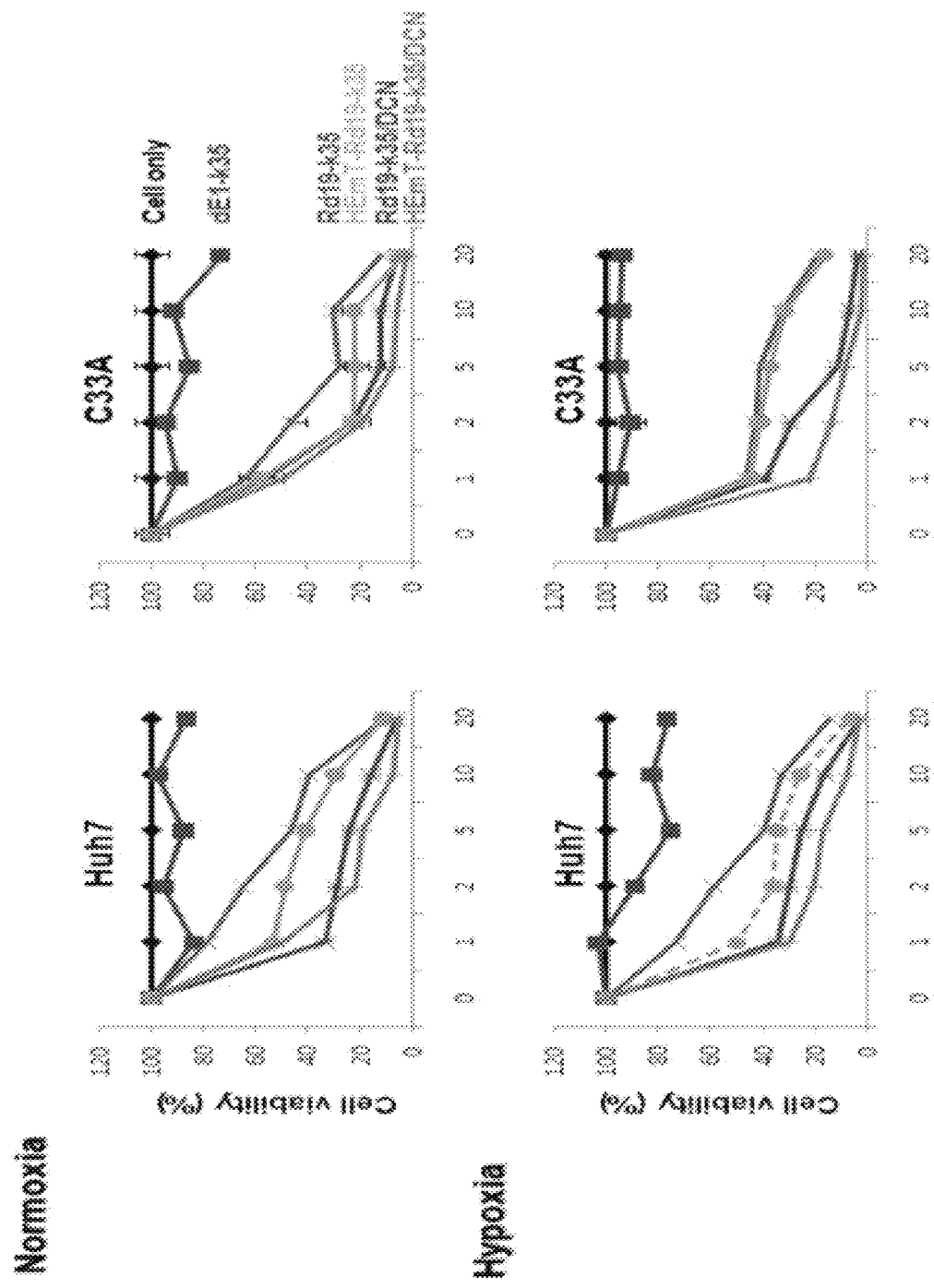

To assess oncolytic activity (cytopathic effect) of Decorin-expressing HEmT-Rd19-k35/DCN oncolytic adenovirus, brain tumor cell lines (U343, U87MG) and other tumor cell lines (Huh7, C33A) were infected by each virus (Rd19-k35, HEmT-Rd19-k35, Rd19-k35/DCN, HEmT-Rd19-k35/DCN) and the cytopathic effect was analyzed (FIG. 16). As shown in FIG. 16, in all tumor cell lines used in the present invention, oncolytic adenovirus in which the viral replication was regulated by HEmT promoter showed stronger the cytopathic effect than the control group Rd19-k35. In addition, it would be appreciated that the cytopathic effect of Decorin-expressing oncolytic adenovirus Rd19-k35/DCN or HEmT-Rd19-k35/DCN was increased than that of the control group Rd19-k35 or HEmT-Rd19-k35, respectively.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A gene expression regulatory sequence, comprising:
   (i) a hypoxia-response elements (HRE) enhancer sequence;
   (ii) an E2F promoter consisting of the nucleotide sequence as set forth in SEQ ID NO: 1, and
   (iii) a telomere reverse transcriptase (TERT) promoter consisting of the nucleotide sequence of as set forth in SEQ ID NO: 3;
   wherein the gene expression regulatory sequence comprises the HRE sequence, the E2F promoter and the TERT promoter sequence in a 5' to 3' direction, and the E2F promoter as set forth in (ii) is contiguously repeated 2 to 10 times, and the HRE enhancer sequence, the E2F promoter sequence and the TERT promoter sequence cooperatively trigger the expression of a gene.

2. The gene expression regulatory sequence of claim 1, wherein the HRE enhancer sequence is contiguously repeated 2 to 20 times.

3. The gene expression regulatory sequence of claim 1, wherein the HRE sequence is contiguously repeated 6 times and the E2F promoter sequence as set forth in (ii) is contiguously repeated 2 times.

4. A gene delivery system with tumor-specific expression, comprising:
   (a) the gene expression regulatory sequence of claim 1; and
   (b) a target gene of interest to be expressed operably linked to the gene expression regulatory sequence.

5. The gene delivery system of claim 4, wherein the gene delivery system is a plasmid, a recombinant adenovirus, an adeno-associated virus, retrovirus, lentivirus, herpes simplex virus, a vaccinia virus, a pox virus, a polymer, a liposome or a niosome.

6. The gene delivery system of claim 5, wherein the gene delivery system is a recombinant adenovirus vector.

7. A recombinant adenovirus with oncolytic activity, comprising:

(a) an adenovirus inverted terminal repeat (ITR) sequence;
   (b) a gene expression regulatory sequence, comprising
     (i) a hypoxia-response elements (HRE) enhancer sequence;
     (ii) an E2F promoter consisting of the nucleotide sequence as set forth in SEQ ID NO: 1; and
     (iii) a telomere reverse transcriptase (TERT) promoter consisting of the nucleotide sequence as set forth in SEQ ID NO: 3;
     wherein the gene expression regulatory sequence comprises the HRE sequence, the E2F promoter and the TERT promoter sequence in a 5' to 3' direction, and the E2F promoter sequence as set forth in (ii) is contiguously repeated 2-10 times, and the HRE enhancer sequence, the E2F promoter sequences and the TERT promoter sequence cooperatively trigger the expression of a gene; and
   (c) a therapeutic transgene to be expressed operably linked to the gene expression regulatory sequence, wherein the therapeutic gene is selected from the group consisting of a tumor suppressor gene, an antigenic gene, a cytotoxic gene, a cytostatic gene, an apoptosis gene and an anti-angiogenic gene.

8. The recombinant adenovirus of claim 7, wherein the HRE sequence in the gene expression regulatory sequence is contiguously repeated 2 to 20 times.

9. The recombinant adenovirus of claim 7, wherein the gene expression regulatory sequence is inserted into E1 region of said recombinant adenovirus vector.

10. The recombinant adenovirus of claim 9, wherein the HRE sequence is contiguously repeated 6 times and the E2F promoter sequence as set forth in (ii) is contiguously repeated 2 times.

11. The recombinant adenovirus of claim 7, wherein the therapeutic transgene is selected from the group consisting of Apolipoprotein Kringle 8 (LK 8) gene, cytosine kinase (CD) gene, thymidine kinase (TK) gene and decorin gene.

* * * * *

SEQUENCE LISTING

```
<160> NUMBER OF SEQ ID NOS: 3

<210> SEQ ID NO 1
<211> LENGTH: 462
<212> TYPE: DNA
<213> ORGANISM: Artificial Sequence
<220> FEATURE:
<223> OTHER INFORMATION: modified E2F promoter

<400> SEQUENCE: 1
atcgataccg tcgaaacttg tttattgcag cttataatgg ttacaaataa agcaatagca      60
tcacaaattt cacaaataaa gcattttttt cactgcattc tagttgtggt ttgtccaaac     120
tcatcaatgt atcttatcat gtctggatcc gctagcggcg cgccgtttca tccggacaaa     180
gcctgcgcgc gccccgcccc gccattggcc gtaccgcccc gcgccgccgc cccatctcgc     240
ccctcgccgc cgggtccggc gcgttaaagc caataggaac cgccgccgtt gttcccgtca     300
cggccggggc agccaattgt ggcggcgctc ggcggctcgt ggctctttcg cggcaaaaag     360
gatttggcgc gtaaaagtgg ccgggacttt gcaggcagcg cggccggggg gcggagcggg     420
atcgagccct cgatgatatc agaaacgata tcaccggtcg ac                        462

<210> SEQ ID NO 2
<211> LENGTH: 41
<212> TYPE: DNA
<213> ORGANISM: Homo sapiens

<400> SEQUENCE: 2
tcgagccaca gtgcatacgt gggctccaac aggtcctctt g                          41

<210> SEQ ID NO 3
<211> LENGTH: 892
<212> TYPE: DNA
<213> ORGANISM: Artificial Sequence
<220> FEATURE:
<223> OTHER INFORMATION: mTERT

<400> SEQUENCE: 3
tctagcatcg atgtcgaggg atctctccgc tggggccctc gctggcgtcc ctgcaccctg      60
ggagcgcgag cggcgcgcgg gcggggaagc gcggcccaga ccccgggtc cgcccggagc      120 agctgcgctg tcggggccag gccgggctcc cagtggattc gcgggcacag acgcccagga     180
ccgcgctccc cacgtggcgg agggactggg gacccgggca cccgtcctgc cccttcacct     240
tccagctccg cctcctccgc gcggaccccg ccccgtcccg acccctcccg ggtccccggc     300
```

```
ccagccccct ccgggccctc ccagccccct cccttcctttt ccgcggcccc gccctctcct      360
cgcggcgcga gtttcaggca gcgctgcgtc ctgctgcgca cgtgggaagc cctggccccg      420 ggcaccccg cgaagcttag gccgattcga gatctctccg ctggggccct cgctggcgtc       480
cctgcaccct gggagcgcga gcggcgcgcg ggcggggaag cgcggcccag accccgggt      540 ccgcccggag cagctgcgct gtcggggcca ggccgggctc ccagtggatt cgcgggcaca      600
gacgcccagg accgcgctcc ccacgtggcg gagggactgg ggacccgggc accgtcctg      660 cccttcacc ttccagctcc gcctcctccg cgcggacccc gccccgtccc gacccctccc      720 gggtcccgg cccagccccc tccgggccct cccagccccct ccccttcctt tccgcggccc     780
cgccctctcc tcgcggcgcg agtttcaggc agcgctgcgt cctgctgcgc acgtgggaag     840
ccctggcccc gggcaccccc gcgaagcttc gaatcgcgaa ttcgccctcg ag            892
```